US008168645B2

(12) United States Patent
Baell et al.

(10) Patent No.: US 8,168,645 B2
(45) Date of Patent: May 1, 2012

(54) ARYLSULFONAMIDE COMPOUNDS

(75) Inventors: Jonathan Bayldon Baell, Bundoora (AU); Guillaume Laurent Lessene, Coburg (AU); Brad Edmund Sleebs, Reservoir (AU); Wayne J. Fairbrother, Burlingame, CA (US); John A. Flygare, Burlingame, CA (US); Michael F. T. Koehler, Palo Alto, CA (US)

(73) Assignee: Genentech, Inc., South San Francisco, CA (US)

( * ) Notice: Subject to any disclaimer, the term of this patent is extended or adjusted under 35 U.S.C. 154(b) by 302 days.

(21) Appl. No.: 12/513,835

(22) PCT Filed: Nov. 15, 2007

(86) PCT No.: PCT/US2007/084873
§ 371 (c)(1),
(2), (4) Date: Nov. 12, 2009

(87) PCT Pub. No.: WO2008/061208
PCT Pub. Date: May 22, 2008

(65) Prior Publication Data
US 2010/0056517 A1    Mar. 4, 2010

Related U.S. Application Data

(60) Provisional application No. 60/859,315, filed on Nov. 15, 2006.

(51) Int. Cl.
*A61K 31/517* (2006.01)
*C07D 239/72* (2006.01)
(52) U.S. Cl. .................................. 514/266.2; 544/293
(58) Field of Classification Search ................. 544/293; 514/266.2
See application file for complete search history.

(56) References Cited

U.S. PATENT DOCUMENTS

| 6,720,338 | B2 | 4/2004 | Augeri et al. |
|---|---|---|---|
| 2002/0086887 | A1 | 7/2002 | Augeri et al. |
| 2005/0159427 | A1 | 7/2005 | Bruncko et al. |
| 2006/0084647 | A1 | 4/2006 | Wang et al. |
| 2006/0128706 | A1 | 6/2006 | Bruncko et al. |
| 2006/0258657 | A1 | 11/2006 | Bruncko et al. |
| 2007/0015787 | A1 | 1/2007 | Bruncko et al. |
| 2007/0027135 | A1 | 2/2007 | Bruncko et al. |
| 2007/0072870 | A2 | 3/2007 | Feenstra et al. |
| 2008/0287419 | A1 | 11/2008 | Bruncko et al. |

FOREIGN PATENT DOCUMENTS

WO    WO 03/080586 A1    10/2003

OTHER PUBLICATIONS (International Search Report and Written Opinion for International Patent Application No. PCT/US2007/084873), 2008.

Chen, L. et al., "Differential targeting of prosurvival Bcl-2 proteins by their BH3-only ligands allows complementary apoptotic function" *Mol. Cell* 17:393-403 (Feb. 4, 2005).
Cory and Adams, "Killing cancer cells by flipping the Bcl-2Bax switch" *Cancer Cell* 8(1):5-6 (Jul. 2005).
Hinds, M.G. et al., "The structure of Bcl-w reveals a role for the C-terminal residues in modulating biological activity" *EMBO Journal* 22(7):1497-1507 (2003).
Liu, X. et al., "The structure of a Bcl-$x_L$/Bim fragment complex: implications for Bim function" *Immunity* 19:341-352 (Sep. 2003).
Muchmore, S.W. et al., "X-ray and NMR structure of human Bcl-$x_L$, an inhibitor of programmed cell death" *Nature* 381:335-341 (May 23, 1996).
Oltersdorf, T. et al., "An inhibitor of Bcl-2 family proteins induces regression of solid tumours" *Nature* 435:677-681 (Jun. 2, 2005).
Petros, A.M. et al. *J. Med. Chem.* 49:656-663 (2006).
Petros, A.M. et al., "Rationale for Bcl-$x_L$/bad peptide complex formation from structure, mutagenesis, and biophysical studies" *Protein Science* 9:2528-2534 (2000).
Sattler, M. et al., "Structure of Bcl-$x_L$-Bak peptide complex: recognition between regulators of apoptosis" *Science* 275:983 (1997).
Wang, J. et al., "Structure-based discovery of an organic compound that binds Bcl-2 protein and induces apoptosis of tumor cells" *Proc. Natl. Acad. Sci. USA* 97(13) :7124-7129 (Jun. 20, 2000)
Wendt et al. *J. Med. Chem.* 49:1165 (2006).
Willis, S.N. et al., "Proapoptotic Bak is sequestered by Mcl-1 and Bcl-$x_L$, but not Bcl-2, until displaced by BH3-only proteins" *Genes Dev.* 19:1294-1305 (2005).
Zhang, Jason Y., "Apoptosis-based anticancer drugs" *Natures Reviews/Drug Discovery* 1:101-102 (Feb. 2002).

*Primary Examiner* — Rebecca Anderson
(74) *Attorney, Agent, or Firm* — Genentech, Inc.; Alex Andrus

(57) ABSTRACT

The invention relates generally to small molecules that mimic the biological activity of certain peptides and proteins, to compositions containing them and to their use. In particular, the invention relates to compounds of the general formula (I) that mimic the biological activity of BH3-only proteins and are capable of binding to and neutralizing pro-survival Bcl-2 proteins:

(I)

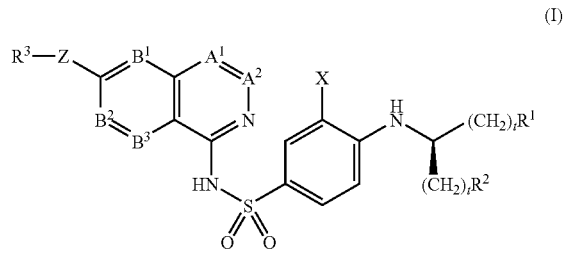

wherein $A^1$, $A^2$, $B^1$, $B^2$, $B^3$, X, Z, $R_1$, $R_2$, $R_3$ and t are as described herein. The invention also relates to processes of preparing the benzenesulfonamide compounds that mimic portions of peptides and proteins, and to the use of such compounds in the regulation of cell death and the treatment and/or prophylaxis of diseases or conditions associated with the deregulation of cell death.

15 Claims, 2 Drawing Sheets

ARYLSULFONAMIDE COMPOUNDS

CROSS REFERENCE TO RELATED APPLICATION

This application is a National Stage of International Application PCT/US2007/084873, filed Nov. 15, 2007, which claims priority under 35 USC §119 to U.S. Provisional Application No. 60/859,315, filed Nov. 15, 2006, the entire contents of which are hereby incorporated by reference.

FIELD OF THE INVENTION

The invention generally relates to novel inhibitors of Bcl-2 family proteins that are useful as therapeutic agents for treating malignancies. The invention also relates to processes of preparing the compounds and compositions useful in the regulation of cell death and the treatment and/or prophylaxis of diseases or conditions associated with the deregulation of cell death.

BACKGROUND OF THE INVENTION

Apoptosis is now recognized as an essential biological process in tissue homeostasis of all living species. In mammals in particular, it has been shown to regulate embryonic development. Later in life, cell death is a default mechanism that removes potentially dangerous cells (e.g. cells carrying cancerous defects). Several apoptotic pathways have been uncovered and one of the most important involves the Bcl-2 family of proteins. The structural homology domains BH1 to BH4 are characteristic of this family. Further classification into of three subfamilies depends on how many of these homology domains a protein contains and on its biological activity (pro- or anti-apoptotic).

The first subgroup contains proteins having all 4 homology domains BH1 to BH4. Their general effect is anti-apoptotic thus preserving the cell from starting a cell death process. Proteins such as Bcl-2, Bcl-w and BCl-$x_L$ are members of this first subgroup. Proteins belonging to the second subgroup have a pro-apoptotic effect and contain the three homology domains BH1 to BH3. The two main representative proteins of this second subgroup are Bax and Bak. Finally, the third subgroup is composed of protein containing only the BH3 domain and members of this subgroup are usually referred to as "BH3-only proteins". Their biological effect on the cell is pro-apoptotic. Bim, Bad, Bmf, and Bid are examples of this third subfamily of proteins.

The delicate balance between the three subgroups is the key to homeostasis of the cells. Recent studies have tried to elucidate the mechanisms involving the Bcl-2 family of proteins that allow a cell to undergo programmed cell death upon receiving intra- or extra-cellular signal. Such a signal induces the activation (post translational or transcriptional) of BH3-only proteins. These proteins are the primary inducers of the cascade that leads to cell death. The BH3-only proteins mainly interact with the Bcl-2 subgroup and stop proteins such as Bcl-2, BCl-$x_L$ or Bcl-w from inhibiting the Bax/Bak subgroup. These later proteins are either already anchored to the mitochondrial membrane or migrate to this membrane. Their activation leads to membrane swelling, release of cytochrome C and downstream activation of effector caspases resulting in apoptosis.

As already mentioned the balance between these proteins is essential to the correct cellular response to various stimuli. Any perturbation of this balance will instigate or worsen major diseases. Thus apoptosis perturbations have been shown to be at the origin of important diseases such as neurodegenerative conditions (up-regulated apoptosis) for example, Alzheimer's disease, or proliferative diseases (down-regulated apoptosis) for example, cancer and autoimmune diseases.

The discovery that several proteins of the Bcl-2 family are involved in the onset of cancerous malignancy has unveiled a completely novel way of targeting this still elusive disease. It has been shown in particular that pro-survival proteins such as Bcl-2 are over-expressed in many cancer types (see Table 1) [Zhang, 2002]. The effect of this deregulation is the survival of altered cells which would have undergone apoptosis in normal conditions. The repetition of these defects associated with unregulated proliferation is thought to be the starting point of cancerous evolution. BH3-only proteins have also been shown to act as tumor suppressors when expressed in diseased animals.

TABLE 1

Bcl-2 over-expression in cancer

| Cancer type | Bcl-2 over-expression |
| --- | --- |
| Hormone-refractory prostate cancer | 90-100% |
| Malignant melanoma | 90% |
| Oestrogen-receptor-positive breast cancer | 80-90% |
| Non-Hodgkin's lymphoma | 50% |
| Colon Cancer | 30-50% |
| Chronic lymphocytic leukaemia | 25-50% |

These findings as well as numerous others have made possible the emergence of new concept in anti-cancer strategies and drug discovery. If an entity mimicking the effect of BH3-only proteins were able to enter the cell and overcome the pro-survival protein over-expression, it could be possible to reset the apoptotic process. This strategy may have the advantage that it may alleviate the problem of drug resistance which is usually a consequence of apoptotic deregulation (abnormal survival).

A considerable effort has been made to understand the structural details of the key interactions between BH3-only proteins and the pro-survival subgroup. Fesik and co-workers have demonstrated in the case of the dimer Bad/Bcl-$x_L$ the importance of some structural elements [Muchmore et. al., 1996; Sattler et. al., 1997 and Petros et. al., 2000]:

binding occurs between a hydrophobic groove located on BCl-$x_L$ and the BH3 domain of Bad;

the BH3-only protein Bad adopts a helix structure upon binding to the hydrophobic groove of BCl-$x_L$; and four hydrophobic amino-acids of the BH3 domain located at i, i+3, i+7 and i+11 intervals are essential to the binding of Bad to BCl-$x_L$ and interact in four hydrophobic pockets situated in the BCl-$x_L$ binding groove. Moreover, studies of members of the BH3-only subgroups have shown that these four hydrophobic amino-acids are conserved through the subgroup.

Recently the structure of the pro-survival protein Bcl-w [Hinds et. al., 2003] and the structure of BH3-only protein Bim in interaction with BCl-$x_L$ [Liu et. al., 2003] have been published. This latter structure confirms the findings of the Bad/Bcl-$x_L$ interaction.

A potential target for new drug therapy is small molecules that mimic the interaction between a BH3-only protein and the Bcl-2 family of proteins. Recently a small molecule BH3- only protein mimetic has been shown to have cytotoxic activity in some cancer cell lines and to enhance the effects of radiation therapy and a number of chemotherapeutic agents [Oltersdorf et. al., 2005; US 2002/0086887; WO 03/080586; U.S. Pat. No. 6,720,338; WO 05/049597; Petros, et al., 2006; Cory and Adams, 2005].

The alpha-helix is a common recognition motif displayed in peptides and proteins. Alpha-helical sequences are often involved in protein-protein interactions, such as enzyme-receptor and antibody-receptor interactions. Targeting these protein-protein interactions is now recognised as one of the major challenges in drug discovery.

There is a need for small molecules which may be easily synthesised and that mimic the activity of BH3-only proteins.

SUMMARY OF THE INVENTION

In an aspect of the invention there are provided compounds of the formula (I):

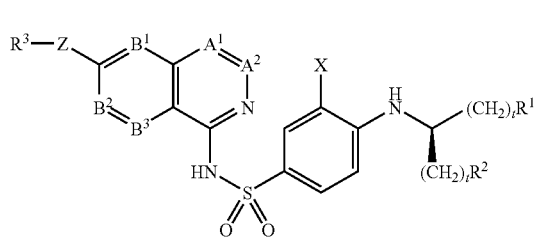

(I)

wherein
X is $NO_2$ or —$SO_2$—$C(X')_3$ wherein X' is H or halo;
$A^1$, $A^2$, $B^1$, $B^2$ and $B^3$ are independently N or $CR^4$;
Z is a cycloalkyl, cycloalkenyl, aryl, heterocyclic or heteroaryl group;
$R^1$ and $R^2$ are independently aryl, heteroaryl, —$NR^5R^6$, —$CONR^5R^6$, —$O(CH_2)_r$aryl, —$O(CH_2)_r$heteroaryl, —$CO(CH_2)_r$aryl, —$CO(CH_2)_r$heteroaryl, —$CO_2(CH_2)_r$aryl, —$CO_2(CH_2)_r$heteroaryl, —$OCO(CH_2)_r$aryl, —$OCO(CH_2)_r$heteroaryl, —$S(CH_2)_r$aryl, —$S(CH_2)_r$heteroaryl, —$SO(CH_2)_r$aryl, —$SO(CH_2)_r$heteroaryl, —$SO_2(CH_2)_r$aryl or —$SO_2(CH_2)_r$heteroaryl;
$R^3$ is alkyl, alkenyl, —$(CH_2)_r$cycloalkyl, —$(CH_2)_r$cycloalkenyl, —$(CH_2)_r$aryl, —$(CH_2)_r$heterocyclyl or —$(CH_2)_r$heteroaryl, wherein each cycloalkyl, cycloalkenyl, aryl, heterocyclyl and heteroaryl may be optionally substituted with alkyl, alkenyl, halo, nitro, haloalkyl, or phenyl optionally substituted with 1, 2 or 3 alkyl, alkenyl, alkoxy, halo or nitro groups;
$R^4$ is hydrogen, halogen, —$C_{1-6}$alkyl, —$C_{2-6}$alkenyl, —$C_{2-6}$alkynyl, hydroxy, —$OC_{1-6}$alkyl, —$OC_{2-6}$alkenyl, —$OC_{2-6}$alkynyl, —$N(R^7)_2$, acyl, —$C(R^8)_3$ or —$CON(R^9)_2$;
$R^5$ and $R^6$ are independently hydrogen, alkyl or alkenyl or $R^5$ and $R^6$ taken together with the nitrogen to which they are attached form a heterocyclic or heteroaryl ring;
each $R^7$ is independently hydrogen, —$C_{1-6}$alkyl, —$C_{2-6}$alkenyl, —$C_{2-6}$alkynyl or acyl;
each $R^8$ is independently hydrogen or halogen;
each $R^9$ is independently hydrogen, —$C_{1-6}$alkyl, —$C_{2-6}$alkenyl or —$C_{2-6}$alkynyl,
t is 0 or an integer 1 to 6; and
r is 0 or an integer 1 to 6;

wherein each alkyl, alkenyl, alkynyl, cycloalkyl, cycloalkenyl, aryl, heterocyclyl and heteroaryl group may be optionally substituted;
or a pharmaceutically acceptable salt thereof.

In another aspect of the present invention, there is provided a method of inducing apoptosis in unwanted or damaged cells comprising contacting said unwanted or damaged cells with an effective amount of a compound of formula (I).

In yet another aspect of the invention there is provided a method of treatment and/or prophylaxis of a pro-survival Bcl-2 member-mediated disease or condition in a mammal, comprising administering to said mammal an effective amount of a compound of formula (I).

In yet another aspect of the invention, there is provided a method of treatment and/or prophylaxis of a disease or condition characterised by inappropriate persistence or proliferation of unwanted or damaged cells in a mammal comprising administering to said mammal an effective amount of a compound of formula (I).

In a further aspect of the invention, there is provided a pharmaceutical composition comprising a compound of formula (I) and at least one pharmaceutically acceptable carrier.

DETAILED DESCRIPTION OF THE INVENTION

Figure 1A:
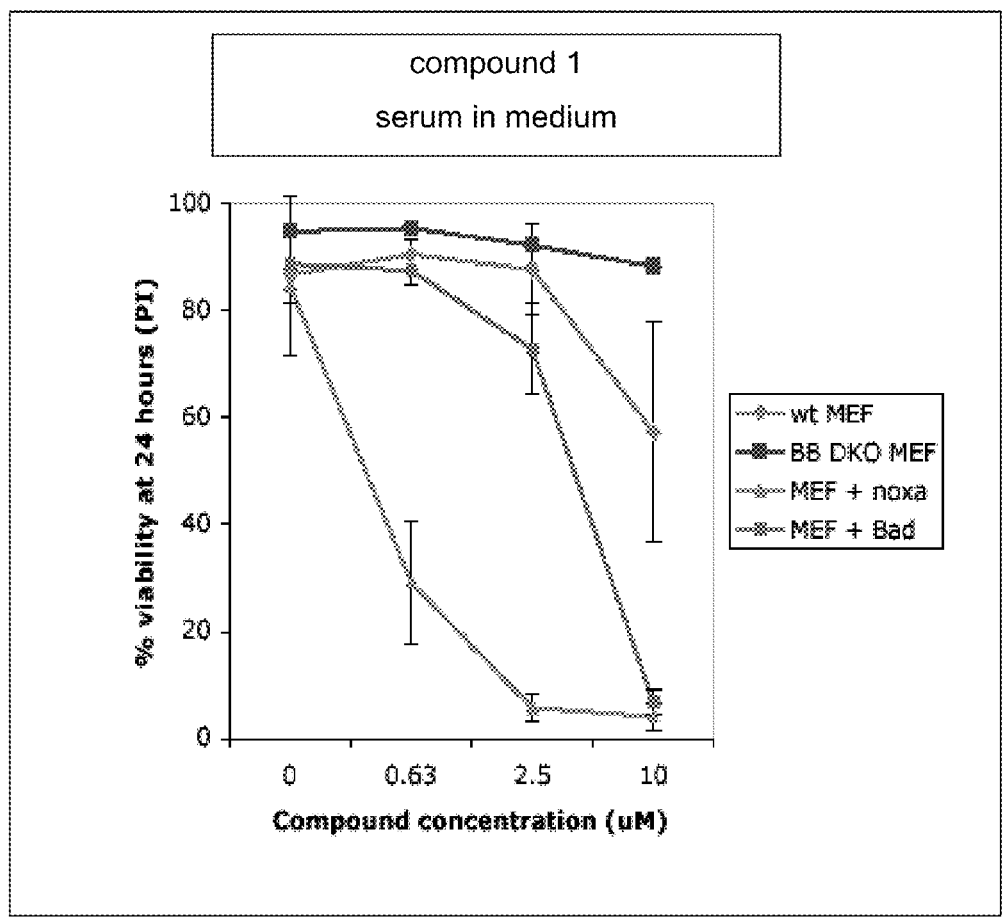
FIG. 1 graphically depicts the effect of Compound 1 (FIG. 1A) and Etoposide (FIG. 1B), at increasing concentrations, on the % viability of certain mouse embryo fibroblast (MEF) cells as assessed by propidium iodide uptake after 24 hours. Noxa and Bad were introduced by retrovirally infecting the cells with pMIG retroviruses as described by Chen et al., 2005.

Throughout this specification and the claims which follow, unless the context requires otherwise, the word "comprise", and variations such as "comprises" and "comprising", will be understood to mean the inclusion of a stated integer or step or group of integers or steps but not the exclusion of any other integer or step or group of integers or steps.

In one aspect of the invention, there is provided a compound of formula (I):

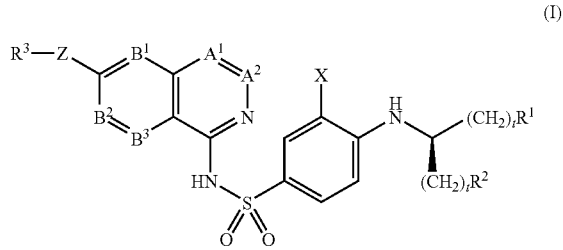

(I)

wherein
X is $NO_2$ or —$SO_2$—$C(X')_3$ wherein X' is H or halo;
$A^1$, $A^2$, $B^1$, $B^2$ and $B^3$ are independently N or $CR^4$;
Z is cycloalkyl, cycloalkenyl, aryl, heterocyclic or heteroaryl group;
$R^1$ and $R^2$ are independently aryl, heteroaryl, —$NR^5R^6$, —$CONR^5R^6$, —$O(CH_2)_r$aryl, —$O(CH_2)_r$heteroaryl, —$CO(CH_2)_r$aryl, —$CO(CH_2)_r$heteroaryl, —$CO_2(CH_2)_r$aryl, —$CO_2(CH_2)_r$heteroaryl, —$OCO(CH_2)_r$aryl, —$OCO(CH_2)_r$heteroaryl, —$S(CH_2)_r$aryl, —S(CH$_2$)$_r$heteroaryl, —SO(CH$_2$)$_r$aryl, —SO(CH$_2$)$_r$heteroaryl, —SO$_2$(CH$_2$)$_r$aryl or —SO$_2$(CH$_2$)$_r$heteroaryl;

R$^3$ is alkyl, alkenyl, —(CH$_2$)$_t$cycloalkyl, —(CH$_2$)$_t$cycloalkenyl, —(CH$_2$)$_t$aryl, —(CH$_2$)$_t$heterocyclyl, or —(CH$_2$)$_t$heteroaryl, wherein each cycloalkyl, cycloalkenyl, aryl, heterocyclyl and heteroaryl may be optionally substituted with alkyl, alkenyl, halo, nitro, haloalkyl, or phenyl optionally substituted with 1, 2 or 3 alkyl, alkenyl, alkoxy, halo or nitro groups;

R$^4$ is hydrogen, halogen, —C$_{1-6}$alkyl, —C$_{2-6}$alkenyl, —C$_{2-6}$alkynyl, hydroxy, —OC$_{1-6}$alkyl, —OC$_{2-6}$alkenyl, —OC$_{2-6}$alkynyl, —N(R$^7$)$_2$, acyl, —C(R$^8$)$_3$ or —CON(R$^9$)$_2$;

R$^5$ and R$^6$ are independently hydrogen, alkyl or alkenyl or R$^5$ and R$^6$ taken together with the nitrogen to which they are attached form a heterocyclic or heteroaryl ring;

each R$^7$ is independently hydrogen, —C$_{1-6}$alkyl, —C$_{2-6}$alkenyl, —C$_{2-6}$alkynyl or acyl;

each R$^8$ is independently hydrogen or halogen;

each R$^9$ is independently hydrogen, —C$_{1-6}$alkyl, —C$_{2-6}$alkenyl and —C$_{2-6}$alkynyl, t is 0 or an integer 1 to 6; and r is 0 or an integer 1 to 6;

wherein each alkyl, alkenyl, alkynyl, cycloalkyl, cycloalkenyl, aryl, heterocyclyl and heteroaryl group may be optionally substituted;

or a pharmaceutically acceptable salt thereof.

As used herein, the term "alkyl" refers to a straight chain or branched saturated hydrocarbon group having 1 to 10 carbon atoms. Where appropriate, the alkyl group may have a specified number of carbon atoms, for example, C$_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl and decyl.

As used herein, the term "alkenyl" refers to a straight-chain or branched hydrocarbon group having one or more double bonds between carbon atoms and having 2 to 10 carbon atoms. Where appropriate, the alkenyl group may have a specified number of carbon atoms. For example, C$_2$-C$_6$ as in "C$_2$-C$_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl and decenyl.

As used herein, the term "alkynyl" refers to a straight-chain or branched hydrocarbon group having one or more triple bonds between carbon atoms and having 2 to 10 carbon atoms. Where appropriate, the alkynyl group may have a specified number of carbon atoms. For example, C$_2$-C$_6$ as in "C$_2$-C$_6$alkynyl" includes groups having 2, 3, 4, 5 or 6 carbon atoms in a linear or branched arrangement. Examples of suitable alkynyl groups include, but are not limited to, ethynyl, propynyl, butynyl, pentynyl, hexynyl, octynyl, nonynyl and decynyl.

As used herein, the term "cycloalkyl" refers to a saturated cyclic hydrocarbon. The cycloalkyl ring may include a specified number of carbon atoms. For example, a 3 to 8 membered cycloalkyl group includes 3, 4, 5, 6, 7 or 8 carbon atoms. Examples of suitable cycloalkyl groups include, but are not limited to, cyclopropyl, cyclobutyl, cyclopentanyl, cyclohexanyl, cycloheptanol and cyclooctanyl.

As used herein, the term "cycloalkenyl" refers to a cyclic hydrocarbon having at least one double bond. The cycloalkenyl ring may include a specified number of carbon atoms. For example, a 4 to 8 membered cycloalkenyl group contains at least one double bond and 4, 5, 6, 7 or 8 carbon atoms. Examples of suitable cycloalkenyl groups include, but are not limited to cyclopentenyl, cyclopenta-1,3-dienyl, cyclohexenyl, cyclohexen-1,3-dienyl, or cyclohexen-1,4-dienyl.

The term "acyl" used herein refers to an alkanoyl or aroyl group as defined by (C=O)R where suitable R groups include, but are not limited to, —C$_{1-7}$alkyl, —C$_{1-7}$alkenyl, —C$_{1-7}$alkynyl, —C$_{3-8}$cycloalkyl, —C$_{3-8}$cycloalkenyl aryl, heterocyclyl, heteroaryl, —C$_{1-7}$alkylaryl, —C$_{1-7}$alkylcycloalkyl, —C$_{1-7}$alkylcycloalkenyl, —C$_{1-7}$alkylheterocyclyl, —C$_{1-7}$alkylheteroaryl, —C$_{1-7}$alkoxyalkyl, —C$_{1-7}$alkylthioalkyl, —C$_{1-7}$alkylthioaryl, —C$_{1-7}$alkoxyaryl and the like.

The terms "alkyloxy" or "alkoxy", "alkenyloxy", "alkynyloxy", "cycloalkyloxy", "cycloalkenyloxy", "aryloxy", "heterocyclyloxy", "heteroaryloxy", "Oalkyl", "Oalkenyl", "Oalkynyl", "Ocycloalkyl", "Ocycloalkenyl", "Oaryl", "Oheterocyclyl" and "Oheteroaryl" as used herein represent an alkyl, alkenyl, alkynyl, cycloalkyl, cycloalkenyl, aryl, heterocyclyl or heteroaryl group as defined attached through an oxygen bridge. Examples of suitable alkyloxy, alkenyloxy, alkynyloxy, cycloalkyloxy, cycloalkenyloxy, aryloxy, heterocyclyloxy and heteroaryloxy groups include, but are not limited to, methoxy, ethoxy, n-propyloxy, n-butyloxy, n-pentyloxy, n-hexyloxy, ethenyloxy, propenyloxy, butenyloxy, pentenyloxy, hexenyloxy, ethynyloxy, propynyloxy, butynyloxy, pentynyloxy, hexynyloxy, cyclopentyloxy, cyclohexyloxy, cyclopentenyloxy, cyclohexenyloxy, phenoxy, naphthoxy, pyrrolidinyloxy, tetrahydrofuranyloxy, furanyloxy and pyridinyloxy.

The terms "alkylthio", "alkenylthio", "alkynylthio", "Salkyl" and "Salkenyl", as used herein represent an alkyl, alkenyl or alkynyl group as defined above attached through a sulfur bridge. Examples of suitable alkylthio, alkenylthio and alkynylthio include, but are not limited to, methylthio, ethylthio, propylthio, butylthio, pentylthio, hexylthio, ethenylthio, propenylthio, butenylthio, pentenylthio, hexenylthio, ethynylthio, propynylthio, butynylthio, pentynylthio and hexynylthio.

As used herein, the term "aryl" is intended to mean any stable, monocyclic or bicyclic carbon ring of up to 7 atoms in each ring, wherein at least one ring is aromatic. Examples of such aryl groups include, but are not limited to, phenyl, naphthyl, tetrahydronaphthyl, indanyl, biphenyl and binaphthyl.

As used herein, the term "halogen" or "halo" refers to fluorine (fluoro), chlorine (chloro), bromine (bromo) and iodine (iodo).

The term "heterocyclic" or "heterocyclyl" as used herein, refers to a cyclic hydrocarbon in which one to four carbon atoms have been replaced by heteroatoms independently N, S or O. A heterocyclic ring may be saturated or unsaturated. Examples of suitable heterocyclyl groups include tetrahydrofuranyl, tetrahydrothiophenyl, pyrrolidinyl, pyrrolinyl, pyranyl, piperidinyl, piperazinyl, pyrazolinyl, dithiolyl, oxathiolyl, dioxanyl, dioxinyl, morpholino, thiomorpholino and oxazinyl.

The term "heteroaryl" as used herein, represents a stable monocyclic or bicyclic ring of up to 7 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, quinoxalinyl, pyrazolyl, indolyl, benzotriazolyl, furanyl, thienyl, thiophenyl, benzothienyl, benzofuranyl, quinolinyl, isoquinolinyl, oxazolyl, isoxazolyl, imidazolyl, pyrazinyl, pyridazinyl, pyridinyl, pyrimidinyl, pyrrolyl, tetrahydroquinoline, thiazolyl, isothiazolyl, 1,2,4-triazolyl, 1,2,4-oxadiazolyl and 1,2,4-thiadiazolyl. Particular heteroaryl groups have 5- or 6-membered rings, such as pyrazolyl, furanyl, thienyl, oxazolyl, isoxazolyl, imidazolyl, pyrazinyl, pyridazinyl, pyridinyl, pyrimidinyl, pyrrolyl, thiazolyl, isothiazolyl, 1,2,4-triazolyl and 1,2,4-oxadiazolyl and 1,2,4-thiadiazolyl.

Each alkyl, alkenyl, alkynyl, cycloalkyl, cycloalkenyl, aryl, heterocyclyl and heteroaryl whether an individual entity or as part of a larger entity may be optionally substituted with one or more optional substituents selected from the group consisting of $C_{1-6}$alkyl, $C_{2-6}$alkenyl, $C_{2-6}$alkynyl, $C_{3-6}$cycloalkyl, $C_{1-6}$alkyloxy$(CH_2)_p$—, $C_{2-6}$alkenyloxy$(CH_2)_p$—, $C_{2-6}$alkynyloxy$(CH_2)_p$—, $C_{3-6}$cycloalkoxy$(CH_2)_p$—, $C_{1-6}$alkylthio$(CH_2)_p$—, $C_{2-6}$alkenylthio$(CH_2)_p$—, $C_{2-6}$alkynylthio$(CH_2)_p$—, $C_{3-6}$cycloalkylthio$(CH_2)_p$—, hydroxy$(CH_2)_p$—, —$(CH_2)_p$SH, —$(CH_2)_p$CO$_2$H, —$(CH_2)_p$CO$_2$C$_{1-6}$alkyl, $(CH_2)_p$CON$(R^{10})_2$, $C_{2-6}$acyl$(CH_2)_p$—, $C_{2-6}$acyloxy$(CH_2)_p$—, $C_{2-6}$alkylSO$_2(CH_2)_p$—, $C_{2-6}$alkenylSO$_2(CH_2)_p$—, $C_{2-6}$alkynylSO$_2(CH_2)_p$—, arylSO$_2$$(CH_2)_p$—, heteroarylSO$_2(CH_2)_p$—, heterocyclylSO$_2$$(CH_2)_p$—, —$(CH_2)_p$NH$_2$, —$(CH_2)_p$NH$(C_{1-6}$alkyl), —$(CH_2)_p$N$(C_{1-6}$alkyl)$_2$, —$(CH_2)_p$NH(phenyl), —$(CH_2)_p$N(phenyl)$_2$, —$(CH_2)_p$NH(acyl), —$(CH_2)_p$N(acyl)(phenyl), —$(CH_2)_p$NH—$(CH_2)_p$—S-aryl, —$(CH_2)_p$N═NHC(O)NH$_2$, —$(CH_2)_p$C$(R^{11})_3$, —$(CH_2)_p$OC$(R^{11})_3$, —$(CH_2)_p$SC$(R^{11})_3$, —$(CH_2)_p$CN, —$(CH_2)_p$NO$_2$, —$(CH_2)_p$halogen, —$(CH_2)_p$heterocyclyl, heterocyclyloxy$(CH_2)_p$—, —$(CH_2)_p$heteroaryl, heteroaryloxy$(CH_2)_p$—, —$(CH_2)_p$aryl, —$(CH_2)_p$C(O)aryl and aryloxy$(CH_2)_p$— wherein each $R^{11}$ is independently hydrogen or halogen; each $R^{10}$ is independently H, $C_{1-6}$alkyl, phenyl or cycloalkyl or the two $R^{10}$ taken together with the nitrogen to which they are attached can form a heterocyclyl or heteroaryl ring; and p is 0 or an integer from 1 to 6. Examples of suitable substituents include, but are not limited to, methyl, ethyl, propyl, isopropyl, butyl, sec-butyl, tert-butyl, vinyl, methoxy, ethoxy, propoxy, isopropoxy, butoxy, methylthio, ethylthio, propylthio, isopropylthio, butylthio, hydroxy, hydroxymethyl, hydroxyethyl, hydroxypropyl, hydroxybutyl, fluoro, chloro, bromo, iodo, cyano, nitro, CO$_2$H, CO$_2$CH$_3$, CH$_2$CO$_2$CH$_3$, trifluoromethyl, trifluoromethoxy, trifluoromethylthio, acetyl, morpholino, amino, methylamino, dimethylamino, phenyl, phenylcarbonyl, NHCOphenyl, NHCObenzyl in which the phenyl ring is optionally substituted with methyl or methoxy, NHCOethylphenyl, NHCOCH$_2$Sphenyl —N═NHC(O)NH$_2$, —CH═C(CN)$_2$ and phenoxy. Particular substituents include fluoro, chloro, methyl, ethyl, propyl, isopropyl, butyl, tert-butyl, methoxy, ethoxy, propoxy, isopropoxy, trifluoromethyl, trifluoromethoxy, cyano, nitro, acetyl, amino, methylamino, dimethylamino, phenyl and benzyl in which the phenyl or benzyl ring is optionally substituted with halo, methyl or methoxy.

The compounds of the invention may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

The compounds and salts of the invention may be presented in the form of a prodrug. The term "prodrug" is used in its broadest sense and encompasses those derivatives that are converted in vivo to the compounds of the invention. Such derivatives would readily occur to those skilled in the art, and include N-α-acyloxy amides, N-(acyloxyalkoxy carbonyl) amine derivatives, esters and α-acryloxyalkyl esters of phenols and alcohols. A prodrug may include modifications to one or more of the functional groups of a compound of the invention.

The term "prodrug" also encompasses the combination of lipids with the compounds of the invention. The presence of lipids may assist in the translocation of the compounds across a cellular membrane and into a cell cytoplasm or nucleus. Suitable lipids include fatty acids which may be linked to the compound by formation of a fatty acid ester. Particular fatty acids include, but are not limited to, lauric acid, caproic acid, palmitic acid and myristic acid.

The phrase "a derivative which is capable of being converted in vivo" as used in relation to another functional group includes all those functional groups or derivatives which upon administration into a mammal may be converted into the stated functional group. Those skilled in the art may readily determine whether a group may be capable of being converted in vivo to another functional group using routine enzymatic or animal studies.

It will also be recognised that compounds of the invention may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

In particular embodiments, at least one of the following applies with respect to the moiety:

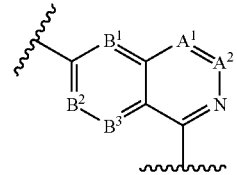

each of $A^1$ and $A^2$ is $CR^4$ or one of $A^1$ and $A^2$ is N and the other is $CR^4$;
each of $B^1$, $B^2$ and $B^3$ is $CR^4$ or one of $B^1$, $B^2$ and $B^3$ is N and the other two are $CR^4$.

In particular embodiments, the moiety:

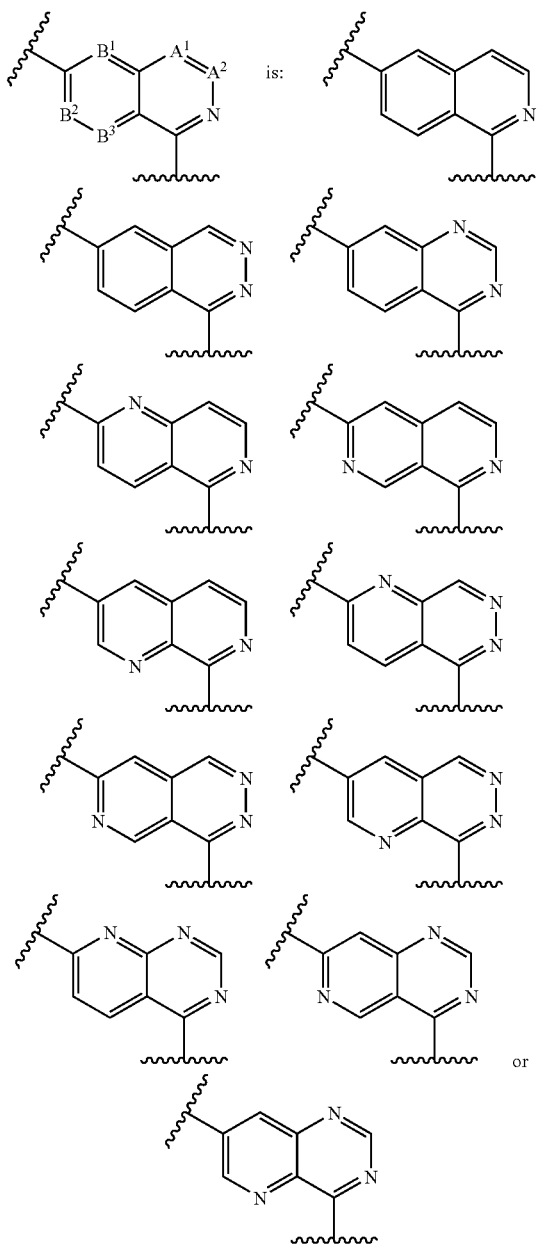

X is NO₂ or —SO₂—C(X')₃ wherein X' is H or halo. In a particular embodiment, X is NO₂ or —SO₂—CF₂X' wherein X' is F or Cl. In a particular embodiment, X is NO₂. In a particular embodiment, X is —SO₂—CF₃. In a particular embodiment, X is —SO₂—CF₂Cl.

Z is a cycloalkyl or heterocyclyl group. In a particular embodiment, Z is a heterocyclyl group. In a particular embodiment, Z is a piperazine group, e.g. piperazin-1-yl.

R¹ and R² are independently aryl, heteroaryl, —NR⁵R⁶, —CONR⁵R⁶, —O(CH₂)ₜaryl, —O(CH₂)ₜheteroaryl, —CO(CH₂)ₜaryl, —CO(CH₂)ₜheteroaryl, —CO₂(CH₂)ₜaryl, —CO₂(CH₂)ₜheteroaryl, —OCO(CH₂)ₜaryl, —OCO(CH₂)ₜheteroaryl, —S(CH₂)ₜaryl, —S(CH₂)ₜheteroaryl, —SO(CH₂)ₜaryl, —SO(CH₂)ₜheteroaryl, —SO₂(CH₂)ₜaryl or —SO₂(CH₂)ₜheteroaryl.

In a particular embodiment, R¹ is aryl, heteroaryl, —S(CH₂)ₜaryl, or —S(CH₂)ₜheteroaryl. In a particular embodiment, R¹ is —S(CH₂)ₜaryl or —S(CH₂)ₜheteroaryl. In a particular embodiment, R¹ is -Saryl or -Sheteroaryl. In a particular embodiment, R¹ is -Sphenyl. In a particular embodiment, the moiety —(CH₂)ₜR¹ is —CH₂—S-phenyl.

In a particular embodiment, R² is —NR⁵R⁶ or —CONR⁵R⁶. In a particular embodiment, R² is —N(alkyl)(alkyl), —CON(alkyl)(alkyl). In a particular embodiment, the group —(CH₂)ₜR² is —CH₂CH₂N(CH₃)₂, —CH₂CON(CH₃)₂.

In a particular embodiment, R² is —NR⁵R⁶ or —CONR⁵R⁶ in which R⁵ and R⁶ together with the nitrogen atom to which they are attached form a heterocyclic or heteroaromatic ring. In a particular embodiment, R⁵ and R⁶ together form a morpholine, piperidine, piperazine or thiomorpholine. In a particular embodiment, the group —(CH₂)ₜR² is —CH₂CH₂(N-morpholine), —CH₂CH₂(N-piperidine), —CH₂CH₂(N-piperazine) and —CH₂CH₂(N-thiomorpholine). In a particular embodiment, the group —(CH₂)ₜR² is —CH₂CH₂(N-azepanyl), —CH₂CH₂(N-oxazapanyl), —CH₂CH₂(N-pyrrolidinyl), —CH₂CH₂(N-7-azabicyclo[2.2.1]heptanyl), —CH₂CH₂(N-2oxa-5-azabicyclo[2.2.1]heptanyl). In a particular embodiment, the group —(CH₂)ₜR² is —CH₂CH₂N(CH₃)₂. In a particular embodiment, the group —(CH₂)ₜR² is —CH₂CH₂(N-morpholine).

R³ is halo, —(CH₂)ₜcycloalkyl, —(CH₂)ₜcycloalkenyl, —(CH₂)ₜaryl, —(CH₂)ₜheterocyclyl, —(CH₂)ₜheteroaryl, wherein each cycloalkyl, cycloalkenyl, aryl, heterocyclyl and heteroaryl may be optionally substituted with alkyl, alkenyl, halo, nitro, haloalkyl, or phenyl optionally substituted with 1, 2 or 3 alkyl, alkenyl, alkoxy, halo or nitro groups. In a particular embodiment, R³ is —(CH₂)ₜaryl optionally substituted with a phenyl group which is optionally substituted at the 4 position with a halo group. In a particular embodiment, R³ is —(CH₂)ₜaryl substituted with a phenyl group which is substituted at the 4 position with a chloro group. In a particular embodiment, R³ is 2-(4-halophenyl)phenylmethyl. In a particular embodiment, R³ is 2-(4-chlorophenyl)phenylmethyl.

In a particular embodiment, R³ is:

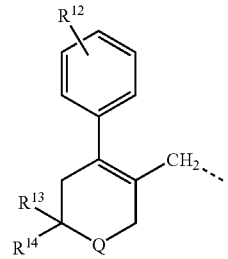

wherein Q is O, CH₂, C(alkyl)₂ or CH₂CH₂; R¹² is halo; and R¹³ and R¹⁴ are both H or are both alkyl. In a particular embodiment, Q is C(CH₃)₂. In a particular embodiment R¹² is Cl. In a particular embodiment, Q is C(CH₃)₂ and R¹³ and R¹⁴ are both H. In a particular embodiment Q is O. In a particular embodiment, Q is O and R¹³ and R¹⁴ are both H. In a particular embodiment, R³ is:

In a particular embodiment, $R^3$ is:

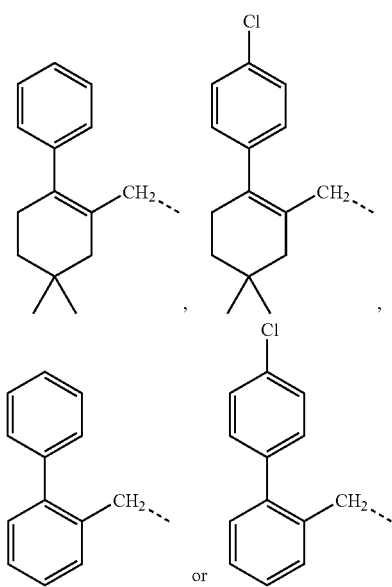

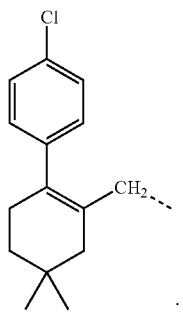

$R^4$ is hydrogen, halogen, —$C_{1-3}$alkyl, —$OC_{1-3}$alkyl, —$NH_2$, —$NH(C_{1-3}$alkyl), —$N(C_{1-3}$alkyl$)_2$, —$NH$(acyl), —$N(C_{1-3}$alkyl)(acyl), acyl, —$CF_3$, —$CONH_2$, —$CONH(C_{1-3}$alkyl) and —$CON(C_{1-3}$alkyl$)_2$. In a particular embodiment $R^4$ is hydrogen, halogen, methyl, methoxy, —$NH_2$, $NHCH_3$, $N(CH_3)_2$, $CF_3$ and $CONH_2$. In a particular embodiment, $R^4$ is hydrogen.

$R^5$ and $R^6$ are independently hydrogen or $C_{1-6}$alkyl. In a particular embodiment, $R^5$ and $R^6$ are independently hydrogen or $C_{1-3}$alkyl. In a particular embodiment, $R^5$ and $R^6$ taken together with the nitrogen to which they are attached form a heterocyclic or heteroaryl ring. In a particular embodiment, $R^5$ and $R^6$ form a heterocyclic ring. In a particular embodiment, $R^5$ and $R^6$ are both methyl. In a particular embodiment, $R^5$ and $R^6$ or together form a morpholine, thiomorpholine, piperidine or piperazine ring. In a particular embodiment, $R^5$ and $R^6$ together form a morpholine ring.

t is 0 or an integer 1 to 5. In a particular embodiment t is 0 or an integer 1 to 3.

r is 0 or an integer 1 to 5. In a particular embodiment, r is 0 or an integer 1 to 3.

In particular embodiments of the invention, the compounds are of formula II:

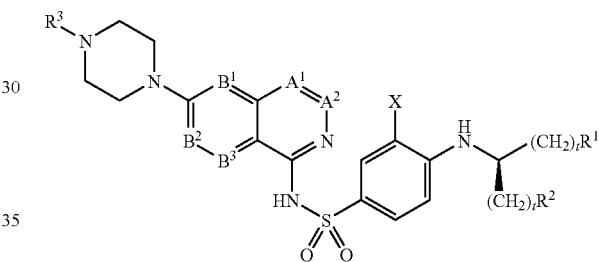

(II)

where X, $A^1$, $A^2$, $B^1$, $B^2$, $B^3$, $R^1$, $R^2$ and $R^3$ are as defined for formula (I).

Particular compounds of the invention include:

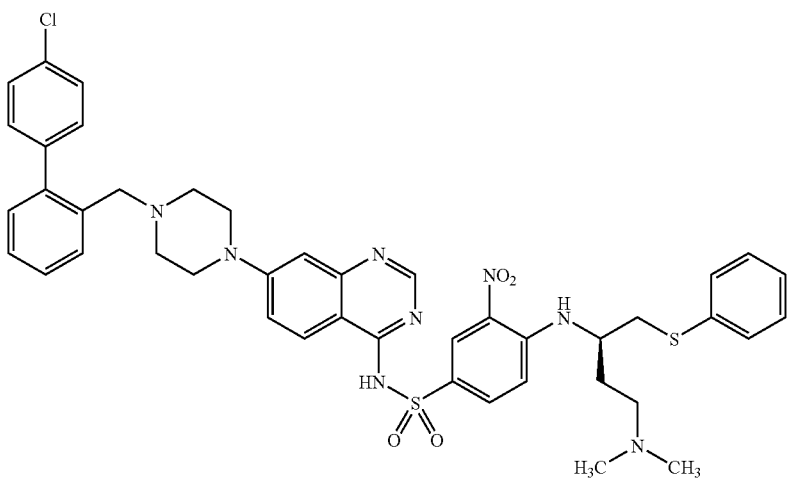

1

-continued
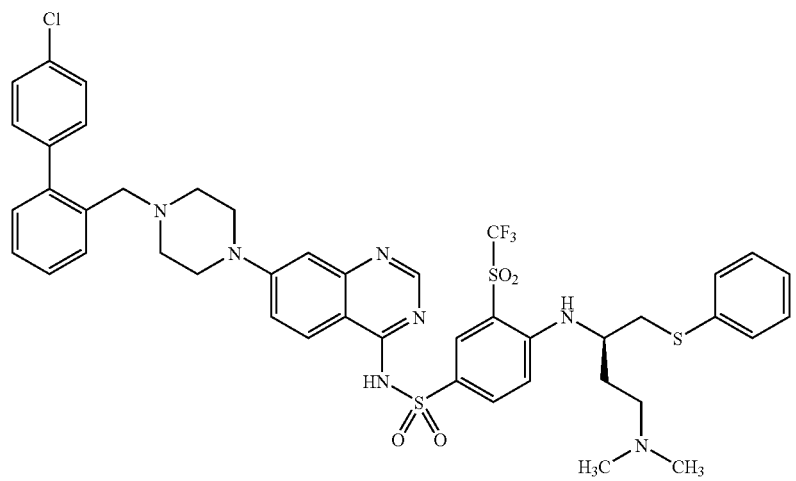
2
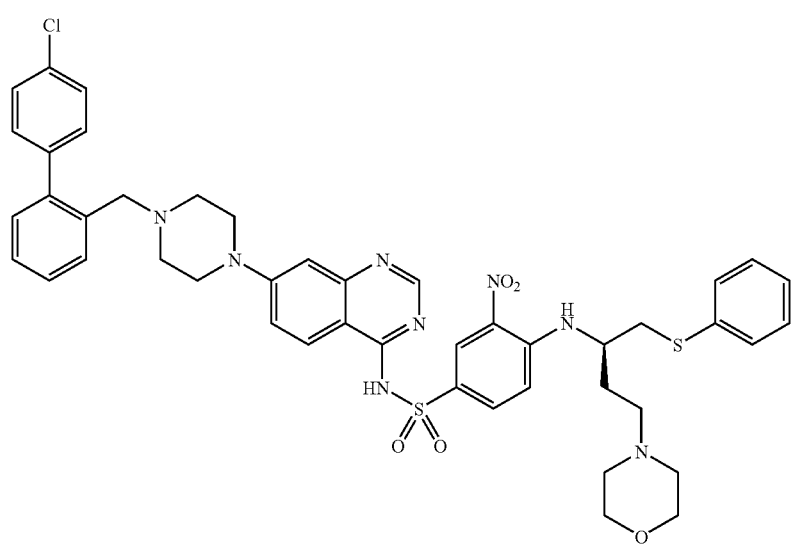
3
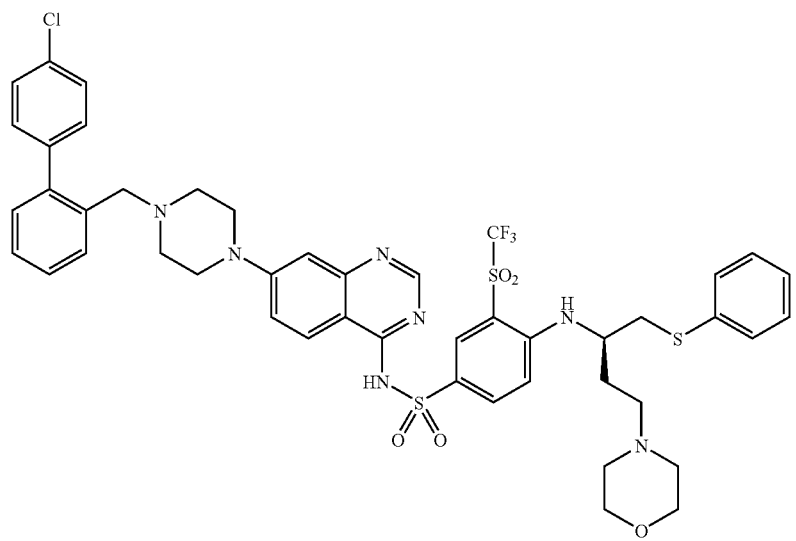
4

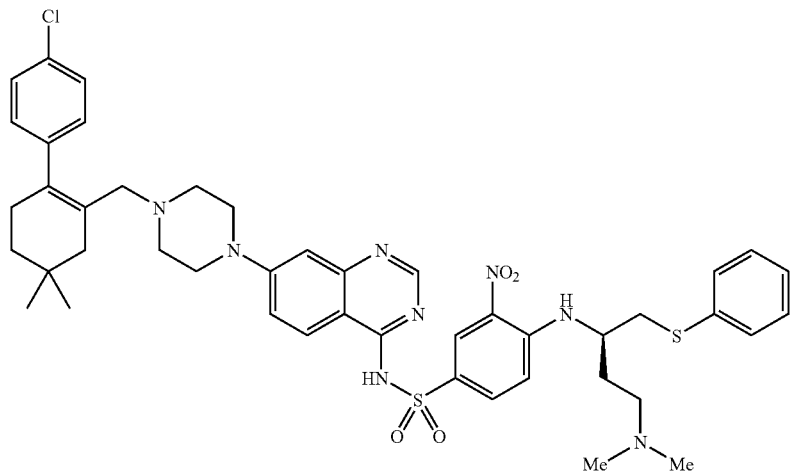
5
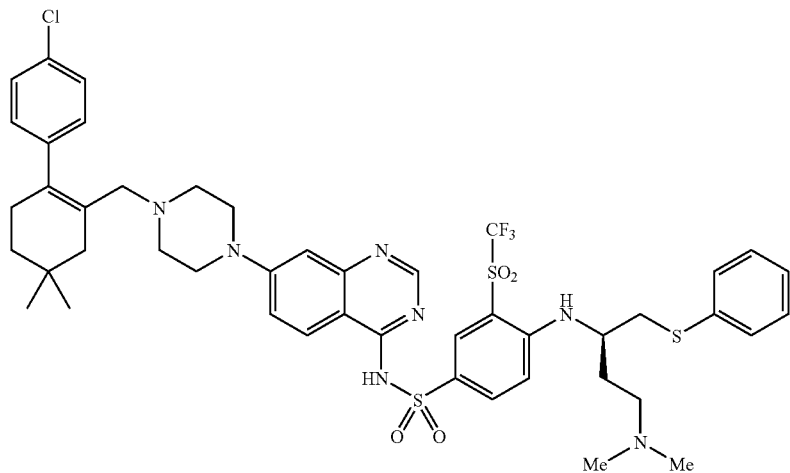
6
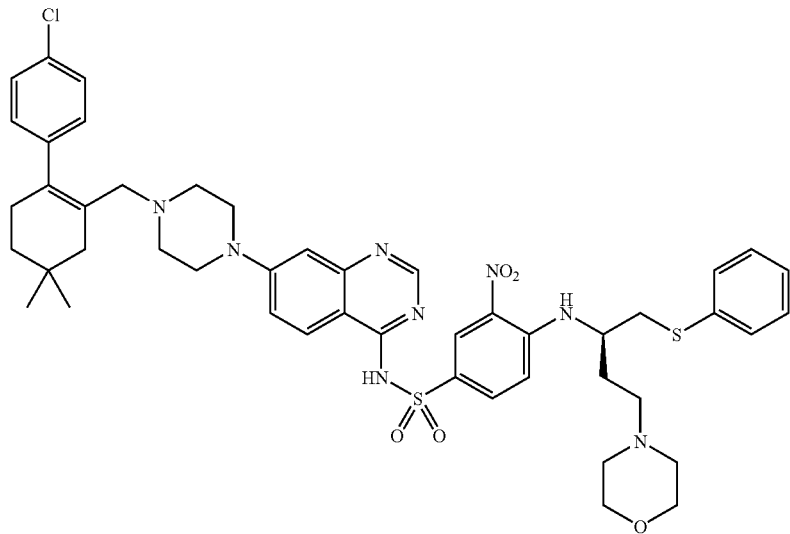
7

8

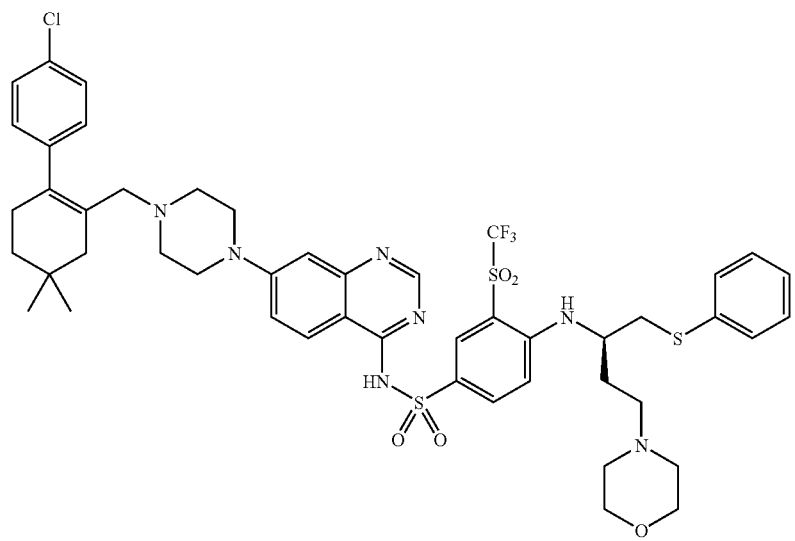

9

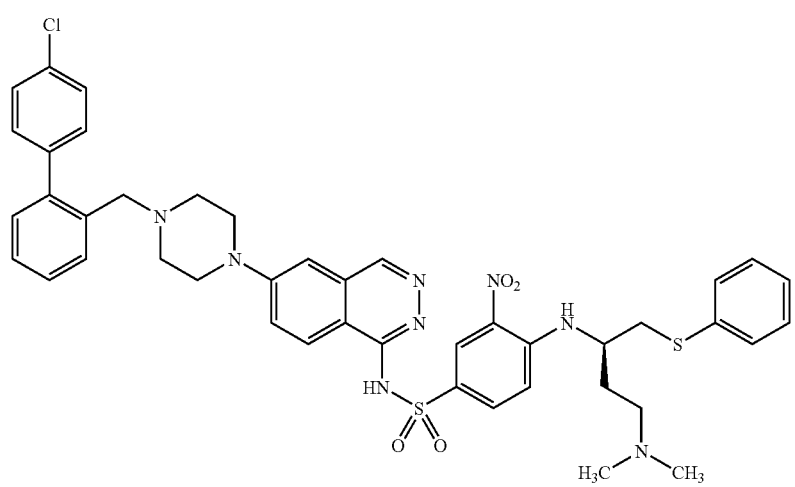

The compounds of the invention may be prepared by synthetic procedures known in the art. One means of preparing the compounds is to use a convergent synthesis, where a substituted arylsulfonamide is prepared and a substituted heterocyclic compound is prepared and then the two molecules are reacted together to form the compound of the invention.

The arylsulfonamide portion of the molecule may be prepared as shown in scheme 1:

The heterocyclic portion of the molecule may be prepared as shown in Scheme 2:

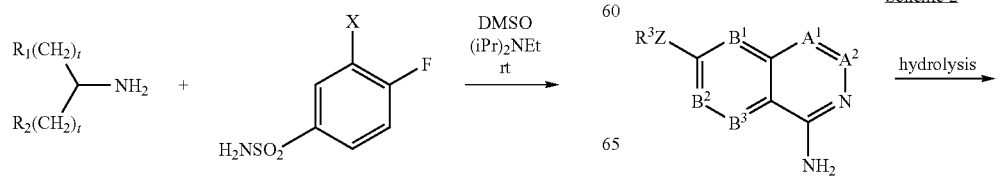

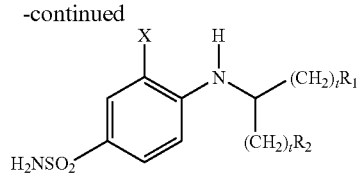

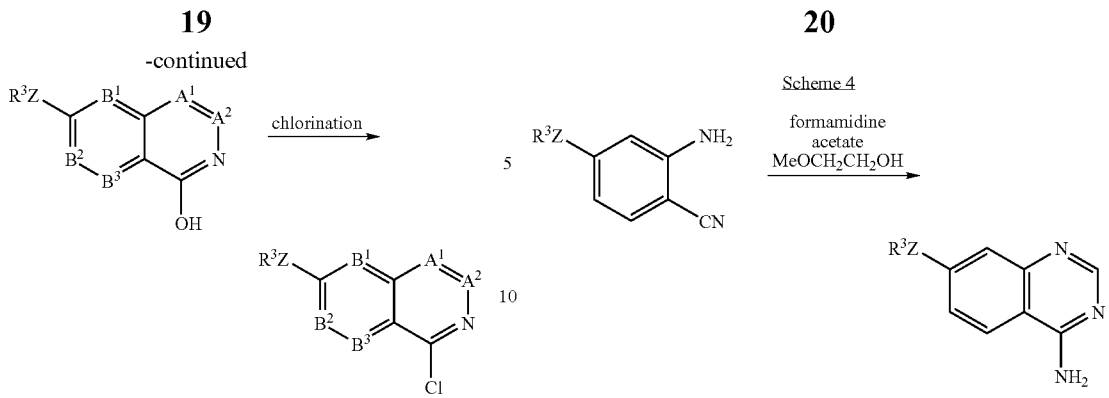

The two parts may be linked together as shown in Scheme 3:

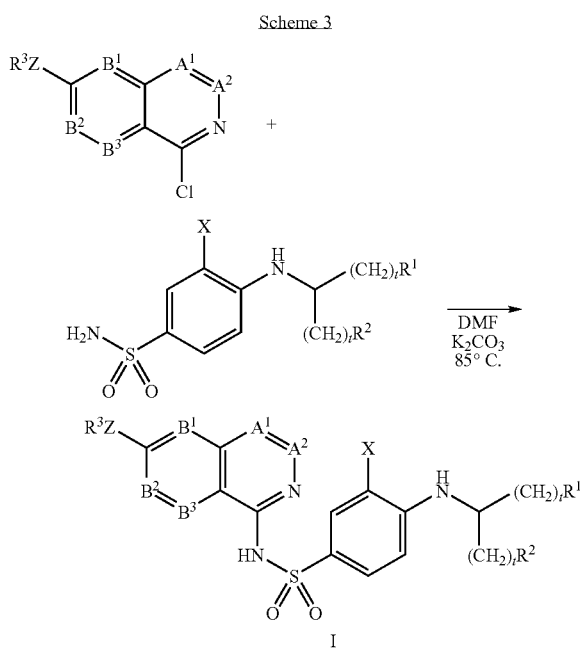

Some compounds of the formulae:

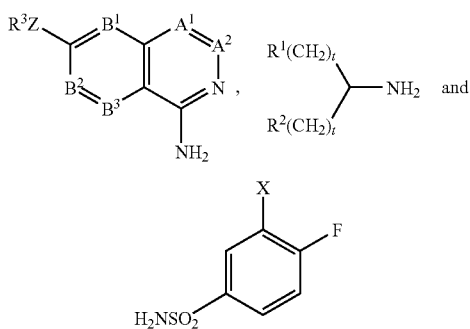

are commercially available, others may be prepared by methods known in the art. For example, a compound in which the heterocyclic moiety includes a quinazoline group may be prepared as shown in Scheme 4:

A person skilled in the art will be aware that during synthesis of the compounds of the invention, some substituents may be reactive under conditions used and must be disguised or protected to prevent unwanted side reactions. Suitable protecting groups for protecting reactive groups from unwanted reactions are provided in Green and Wuts, Protective Groups in Organic Synthesis.

In another aspect of the present invention, there is provided a method of regulating the death of a cell comprising contacting said cell with an effective amount of a compound of Formula (I) as defined herein.

In another aspect of the present invention, there is provided a method of inducing apoptosis in unwanted or damaged cells comprising contacting said unwanted or damaged cells with an effective amount of a compound of formula (I) as defined herein.

The cell which is treated according to a method of the present invention may be located ex vivo or in vivo. By "ex vivo" is meant that the cell has been removed from the body of a subject wherein the modulation of its activity will be initiated in vitro. For example, the cell may be a cell which is to be used as a model for studying any one or more aspects of the pathogenesis of conditions which are characterised by aberrant cell death signalling. In a particular embodiment, the subject cell is located in vivo.

In yet another aspect of the invention there is provided a method of treatment and/or prophylaxis of a pro-survival Bcl-2 member-mediated disease or condition in a mammal, comprising administering to said mammal an effective amount of a compound of formula (I) as defined herein.

In yet another aspect of the invention, there is provided a method of treatment and/or prophylaxis of a disease or condition characterised by inappropriate persistence or proliferation of unwanted or damaged cells in a mammal comprising administering to said mammal an effective amount of a compound of formula (I) as defined herein.

In still another aspect of the invention, there is provided a use of a compound of formula (I) as defined herein in the manufacture of a medicament for the treatment and/or prophylaxis of a pro-survival Bcl-2 family member-mediated disease or condition, or for the treatment and/or prophylaxis of a disease or condition characterised by inappropriate persistence or proliferation of unwanted or damaged cells.

The term "mammal" as used herein includes humans, primates, livestock animals (e.g. sheep, pigs, cattle, horses, donkeys), laboratory test animals (e.g. mice, rabbits, rats, guinea pigs), companion animals (e.g. dogs, cats) and captive wild animals (e.g. foxes, kangaroos, deer). In a particular embodiment, the mammal is human or a laboratory test animal. In a particular embodiment, the mammal is a human.

As used herein, the term "pro-survival Bcl-2 family member-mediated disease or condition" refers to diseases or conditions where unwanted or damaged cells are not removed by normal cellular process, or diseases or conditions in which cells undergo aberrant, unwanted or inappropriate proliferation. Such diseases include those related to inactivation of apoptosis (cell death), including disorders characterised by inappropriate cell proliferation. Disorders characterised by inappropriate cell proliferation include, for example, inflammatory conditions such as inflammation arising from acute tissue injury including, for example, acute lung injury, cancer including lymphomas, such as prostate hyperplasia, genotypic tumours, autoimmune disorders, tissue hypertrophy etc. For example, diseases or conditions associated with or characterised by inappropriate persistence or proliferation of unwanted or damaged cells include those relating to unwanted or damaged B cells, for example B cell non-Hodgkin's lymphoma, B cell acute lymphoblastic leukemia, rheumatoid arthritis, systemic Lupus erythematosis and related arthropathies. Diseases and conditions associated with or characterised by the inappropriate persistence of unwanted or damaged T cells include T cell acute lymphoblastic leukemia, T cell non-Hodgkin's lymphoma and graft vs Host disease. Diseases and conditions associated with or characterised by the inappropriate persistence of unwanted or damaged myeloid cells include acute myelogenous leukemia, chronic myelogenous leukemia and chronic myelomonocytic leukemia. Diseases and conditions associated with or characterised by the inappropriate persistence of unwanted or damaged plasma cells include multiple myeloma. Diseases and conditions associated with or characterised by the inappropriate persistence of unwanted or damaged cancer cells, include cancers, especially ovarian cancer, breast cancer and prostate cancer cells.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. In a particular embodiment, the dosage is in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

The present invention further contemplates a combination of therapies, such as the administration of the compounds of the invention or pharmaceutically acceptable salts or prodrugs thereof together with the subjection of the mammal to other agents or procedures which are useful in the treatment of diseases and conditions characterised by the inappropriate persistence or proliferation of unwanted or damaged cells. For example, the compounds of the present invention may be administered in combination with other chemotherapeutic drugs, or with other treatments such as radiotherapy. Suitable chemotherapeutic drugs include, but are not limited to, cyclophosphamide, doxorubicine, etoposide phosphate, paclitaxel, topotecan, camptothecins, 5-fluorouracil, tamoxifen, staurosporine, avastin, erbitux, imatinib and vincristine.

For use in therapy, a compound of the invention may be administered as a neat chemical. In a particular embodiment the compound of the invention is administered in a pharmaceutical composition.

Thus, in a further aspect of the invention, there is provided a pharmaceutical composition comprising a compound of formula (I) as defined herein and at least one pharmaceutically acceptable carrier. The carrier(s) must be "acceptable" in the sense of being compatible with the other ingredients of the composition and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier, excipient, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to two hundred (200) milligrams, per tablet, are accordingly suitable representative unit dosage forms. The compounds of the present invention can be administered in a wide variety of oral and parenteral dosage forms. It will be obvious to those skilled in the art that the following dosage forms may comprise, as the active component, either a compound of the invention or a pharmaceutically acceptable salt or derivative of the compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

In a particular embodiment, the powders and tablets contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, prefilled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomizing spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 10 microns or less. Such a particle size may be obtained by means known in the art, for example by micronization.

When desired, formulations adapted to give sustained release of the active ingredient may be employed.

In a particular embodiment, the pharmaceutical preparations are in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Particular pharmaceutical compositions are liquids or powders for intranasal administration, tablets or capsules for oral administration, and liquids for intravenous administration.

The invention will now be described with reference to the following Examples which illustrate some particular aspects and embodiments of the present invention. However, it is to be understood that the particularity of the following description of the invention is not to supersede the generality of the preceding description of the invention.

EXAMPLES

Example 1

4-fluoro-3-(trifluoromethylsulfonyl)benzenesulfonamide

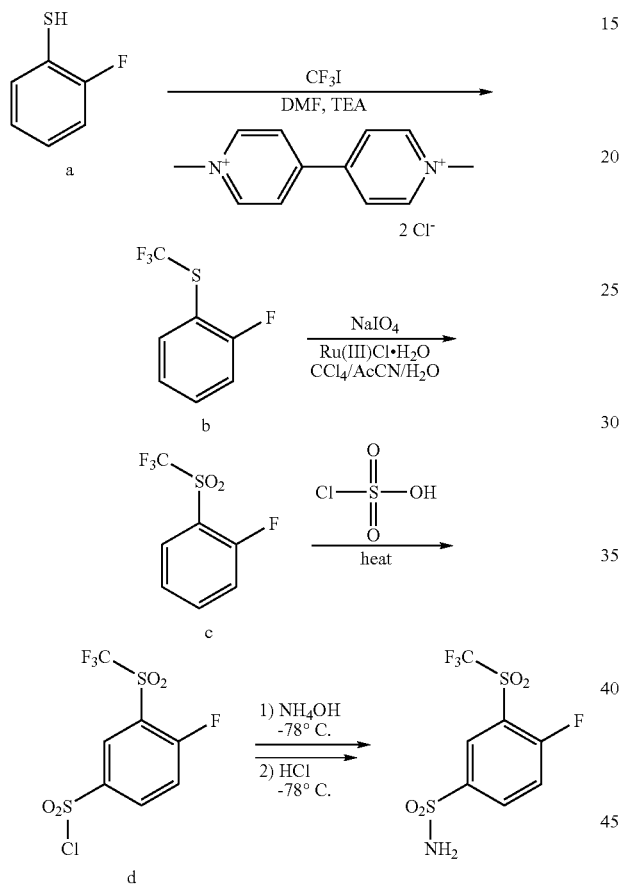

Intermediate 4-fluoro-3-(trifluoromethylsulfonyl)benzenesulfonamide was prepared according to the procedures described in United States patent publication number US2007/0027135. Methyl viologen hydrochloride (0.51 g) in DMF (35 mL) at 25° C. was saturated with trifluoromethyl iodide, treated with 2-fluorobenzenethiol a (5.1 g, 4.24 mL) and TEA (8.8 mL), stirred for 22 hours, diluted with water (240 mL) and extracted with diethyl ether. The extract was washed with 1M NaOH, saturated ammonium chloride and brine and concentrated to give 5.33 g of intermediate b (68% yield).

Intermediate b (5.33 g) in 1:1:2 carbon tetrachloride/acetonitrile/water (336 mL) at 25° C. was treated with sodium periodate (23.86 g) and ruthenium(III)chloride hydrate (77 mg), stirred for 18 hours, diluted with dichloromethane (50 mL) and filtered through diatomaceous earth (Celite®). The filtrate was washed with saturated sodium bicarbonate and extracted with dichloromethane. The extract was washed with brine and dried (MgSO$_4$), filtered and concentrated. The concentrate was filtered through silica gel to give 6.52 g of intermediate c (77% yield).

Intermediate c (6.42 g) in chlorosulfonic acid (5.6 mL) at 120° C. was stirred for 18 hours, cooled to 25° C. and pipetted onto crushed ice. The mixture was extracted with ethyl acetate, and the extract was washed with water and brine and dried (MgSO$_4$), filtered and concentrated to give 5.71 g of intermediate d (62% yield).

Intermediate d (5.71 g) in isopropanol (175 mL) at −78° C. was treated with ammonium hydroxide (24 mL) over 1 hour, stirred for 1 hour, quenched with 6M HCl (88 mL), warmed to 25° C. and concentrated. The concentrate was mixed with water and extracted with ethyl acetate. The extract was dried (MgSO$_4$), filtered and concentrated. The concentrate was recrystallized from ethyl acetate/hexane to give 4.33 g of intermediate 4-fluoro-3-(trifluoromethylsulfonyl)benzenesulfonamide (80% yield).

Example 2

(R)-4-(4-morpholino-1-(phenylthio)butan-2-ylamino)-3-nitrobenzene-sulfonamide

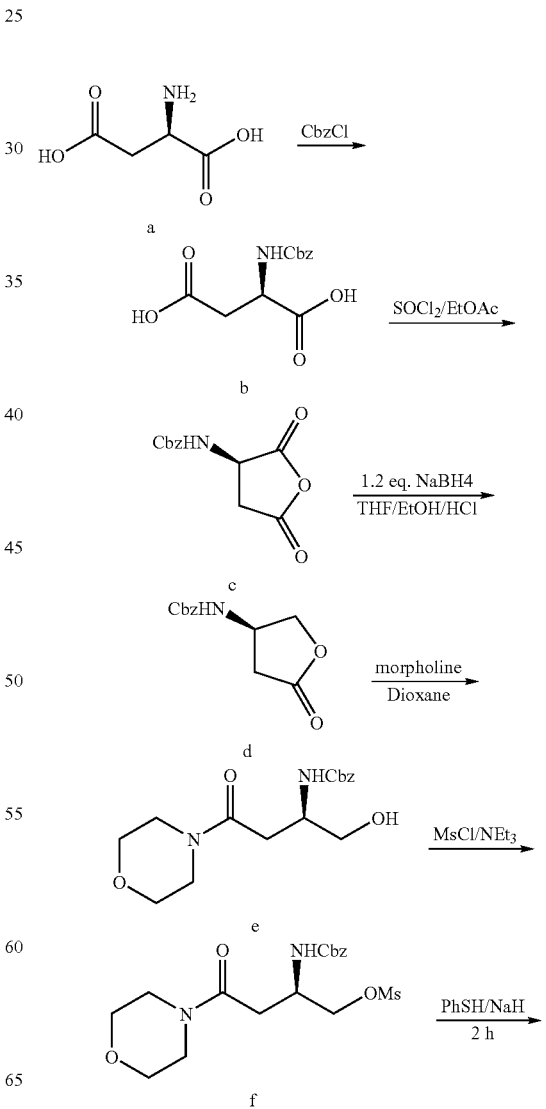

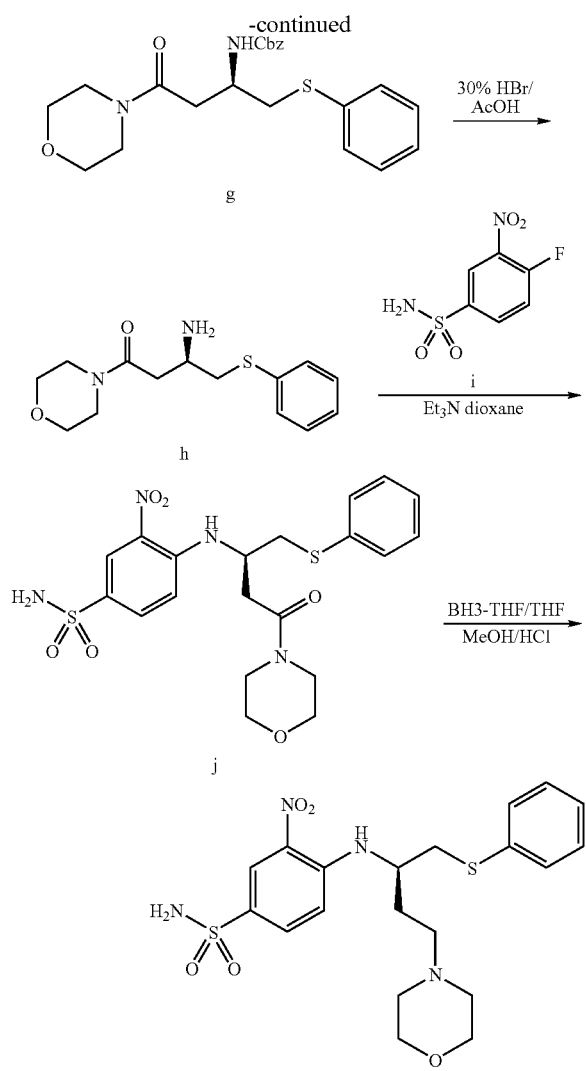

A solution of NaOH (6M, 500 ml) in distilled H₂O was added with (R)-aspartic acid a (65 g, 489 mmol) to adjust the pH=13 of the solution at 0° C., then added with 1.7 eq of benzyl chloroformate (141 g, 831 mmol) under magnetic stirring. The mixture was warmed at room temperature and reacted for 2 days. Subsequently, the mixture was washed with ether and the aqueous phase was acidified with 6N HCl, then extracted with AcOEt. Finally, the organic phase was dried over dry Na₂SO₄, filtered through paper filter and concentrated in rotary evaporator. 80 g of product b in the form of a transparent, colorless gluey residue was obtained (yield: 59%). MS (ESI) m/e (M−H⁻): 266; ¹H-NMR (CDCl₃, 400 MHz): δ 7.27-7.21 (m, 5H), 6.14 (d, J=8.4 Hz, 1H), 5.05 (s, 2H), 4.60 (m, 1H), 2.99 (m, 1H), 2.75 (m, 1H).

A stirred suspension of intermediate b (80 g, 300 mmol) in EtOAc (500 mL) was treated dropwise with thionyl chloride (71 g, 600 mmol) and the resulting homogeneous mixture was stirred at room temperature for 16 hours, and concentrated. The resulting solid was triturated in 1:1 diethyl ether/hexanes for 2 hours and filtered. The solid was dried to provide the desired product c (60 g, yield: 80%). MS (ESI) m/e (M+H⁺): 250.

A stirred suspension NaBH₄ (5.8 g, 154 mmol) in THF (100 mL) was cooled to 0° C., treated dropwise with a solution of compound c (32 g, 128 mmol) in 50 mL of THF, allowed to warm to room temperature, and stirred for 2 hours, The resulting mixture was treated with concentrated HCl (26.2 mL) and ethanol (26.2 mL), heated to reflux for 12 hours, allowed to cool to room temperature, poured into brine and the layers were separated. The aqueous layer was extracted with EA and the combined extracts were dried, filtered, concentrated and purified by silica provide the desired product d (17 g, yield: 57%) MS (ESI) m/e (M+H⁺): 236; ¹H-NMR (CDCl₃, 400 MHz): δ 7.33-7.28 (m, 5H), 5.32 (m, 1H), 5.09 (s, 2H), 4.49 (br s, 2H), 4.22 (m, 1H), 2.84 (dd, J=7.618 Hz, 1H), 2.45 (dd, J=2.8 17.6 Hz, 1H).

A solution of intermediate d (27 g, 115 mmol) and morpholine (20 g, 230 mmol) in 200 mL of dioxane was stirred at 70° C. for 18 hours and concentrated, EtOAc (500 ml) was added and washed with brine, dried over Na₂SO₄ and concentrated to afford the product e as an oil, which was used for the next step without further purification (31 g, 84%). MS (ESI) m/e (M+H⁺):323; ¹H-NMR (CDCl₃, 400 MHz): δ 7.38-7.31 (m, 5H), 5.85 (m, 1H), 5.12 (br s, 2H), 3.92 (m, 1H), 3.71-3.49 (m, 10H), 2.91 (m, 1H), 2.50 (m, 1H).

To a solution of intermediate e (20 g, 62 mmol) and triethylamine (6.9 g, 68 mmol) in dry DCM (300 mL) was added methanesulfonyl chloride (7.9 g, 68 mmol) (diluted 1:1 in DCM) with the temperature maintained <10° C. After the addition, the reaction was stirred for 1 hour at 0° C. Upon completion, the reaction was quenched with water (50 mL). The aqueous layer was cut and the organic layer was dried over Na₂SO₄. The solvent was removed under vacuum to give the product f as a yellow oil, which was used for the next step without purification. MS (ESI) m/e (M+H⁺):401;

To a solution of PhSH (7.5 g, 68 mmol) in dry THF (300 mL) was added NaH (2.7 g, 68 mmol) by portion in ice-water batch with the temperature maintained <10° C. for 1 hour, then the solution of intermediate f was added dropwise, the reaction was stirred for another 1.5 hours at rt. Upon completion, the reaction was quenched with water (100 mL) and EtOAc (200 mL). The aqueous layer was cut and the organic layer was washed with brine, dried over Na₂SO₄. The solvent was removed under vacuum to give the crude product, which was purified by column to afford 12 g of the desired intermediate g. (yield: 47%). MS (ESI) m/e (M+H⁺):415.

A solution of intermediate g 4 g, 9.7 mmol) in 30% HBr in acetic acid (40 ml) was stirred for 24 hours at room temperature, concentrated to half its volume, poured into 1M HCl (40 ml). The combined aqueous layers were washed with ether (3×50 mL) and cooled to 0° C., adjusted to 12 with solid KOH, and extracted with CH₂Cl₂. The combined extracts were washed with brine, dried (Na₂SO₄), filtered, and concentrated to provide the desired product h (2.5 g, yield: 93%). MS (ESI) m/e (M+H⁺):281; ¹H-NMR (CDCl₃, 400 MHz): δ 7.31 (d, J=8.0 Hz, 2H), 7.21 (t, J=7.6 Hz, 2H), 7.12 (t, J=7.6 Hz, 1H), 3.58-3.50 (m, 6H), 3.38-3.30 (m, 3H), 3.05 (m, 1H), 2.87 (m, 1H), 2.50 (m, 1H), 2.28 (m, 1H).

A solution of intermediate h (2.5 g, 8.9 mmol) and intermediate i (1.96 g, 8.9 mmol) in 100 ml of dioxane was treated with Et₃N (1.8 g, 17.8 mmol) heated to reflux overnight, concentrated, and purified by silica gel chromatography eluting with PE:EA=(1:1) to provide the desired product i (3.6 g, yield: 84%). MS (ESI) m/e (M+H⁺): 481; ¹H-NMR (DMSO, 400 MHz): δ 8.66 (d, J=9.6 Hz, 1H), 8.35 (s, 1H), 7.69 (d, J=8.8 Hz, 1H), 7.41-7.21 (m, 5H), 7.15 (m, 1H), 7.05 (d, J=9.6 Hz, 1H), 4.39 (m, 1H), 3.52-3.36 (m, 10H), 2.96 (m, 1H), 2.76 (m, 1H).

A solution of intermediate j (2.0 g, 4.2 mmol) in 100 mL of dry THF was heated to 55° C. and treated dropwise with a solution of 1M borane (19 mL) in THF over a 1 hour period. The resulting reaction mixture was stirred at 55° C. for 18 hours, cooled to 0° C., treated dropwise with methanol, and concentrated. The crude residue was dissolved in methanol, treated with methanolic HCl, and heated to reflux for 24 hours. The mixture was allowed to cool to room temperature, concentrated, diluted with 2M NaOH, and extracted with EtOAc. The combined extracts were washed with 1M NaOH and brine, dried, filtered, concentrated and purified by silica chromatography eluting with $CH_2Cl_2$: MeOH=(10:1) to provide the desired intermediate (R)-4-(4-morpholino-1-(phenylthio)butan-2-ylamino)-3-nitrobenzene-sulfonamide (1.3 g, yield: 66%). MS (ESI) m/e (M+H$^+$): 467; $^1$H-NMR (DMSO, 400 MHz): δ 8.38 (d, J=9.2 Hz, 1H), 8.37 (s, 1H), 7.68 (d, J=9.2 Hz, 1H), 7.29-7.26 (m, 3H), 7.23 (t, J=7.6 Hz, 2H), 7.16 (d, J=7.6 Hz, 1H), 7.09 (d, J=9.6 Hz, 1H), 4.13 (m, 1H), 3.48 (br s, 4H), 3.36 (m, 2H), 2.43 (br s, 4H), 2.18 (br s, 2H), 2.49 (m, 2H), 1.93 (m, 1H), 1.82 (m, 1H).

Example 3

(R)-4-(4-(dimethylamino)-1-(phenylthio)butan-2-ylamino)-3-nitrobenzenesulfonamide

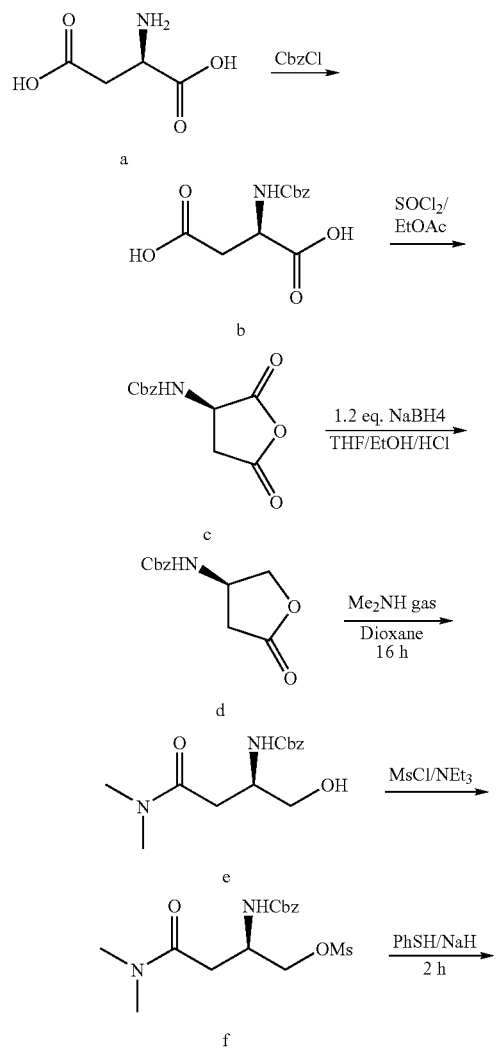

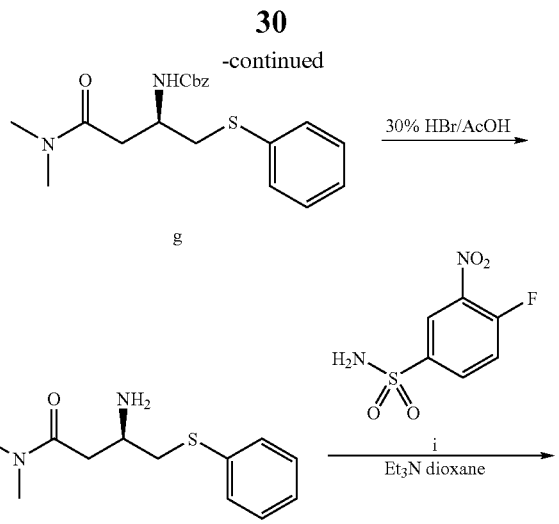

A solution of NaOH (6M, 500 ml) in distilled $H_2O$ was added with (R)-aspartic acid a (65 g, 489 mmol) to adjust the pH=13 of the solution at 0° C., then added with 1.7 eq of benzyl chloroformate (141 g, 831 mmol) under magnetic stirring. The mixture was warmed at room temperature and reacted for 2 days. Subsequently, the mixture was washed with ether and the aqueous phase was acidified with 6N HCl, then extracted with AcOEt. Finally, the organic phase was dried over dry $Na_2SO_4$, filtered through paper filter and concentrated in rotary evaporator. 80 g of product b in the form of a transparent, colorless gluey residue was obtained (yield: 59%). MS (ESI) m/e (M−H$^−$): 266; $^1$H-NMR (CDCl$_3$, 400 MHz): δ 7.27-7.21 (m, 5H), 6.14 (d, J=8.4 Hz, 1H), 5.05 (s, 2H), 4.60 (m, 1H), 2.99 (m, 1H), 2.75 (m, 1H).

A stirred suspension of compound b (80 g, 300 mmol) in EtOAc (500 mL) was treated dropwise with thionyl chloride (71 g, 600 mmol) and the resulting homogeneous mixture was stirred at room temperature for 16 hours, and concentrated. The resulting solid was triturated in 1:1 diethyl ether/hexanes for 2 hours and filtered. The solid was dried to provide the desired product c (60 g, yield: 80%). MS (ESI) m/e (M+H$^+$): 250.

A stirred suspension NaBH$_4$ (5.8 g, 154 mmol) in THF (100 mL) was cooled to 0° C., treated dropwise with a solution of compound c (32 g, 128 mmol) in 50 mL of THF, allowed to warm to room temperature, and stirred for 2 hours. The resulting mixture was treated with concentrated HCl (26.2 mL) and ethanol (26.2 mL), heated to reflux for 12 hours, allowed to cool to room temperature, poured into brine and the layers were separated. The aqueous layer was extracted with EA and the combined extracts were dried, filtered, concentrated and purified by silica provide the desired product d (17 g, yield: 57%) MS (ESI) m/e (M−H⁻): 236; ¹H-NMR (CDCl₃, 400 MHz): δ 7.33-7.28 (m, 5H), 5.32 (m, 1H), 5.09 (s, 2H), 4.49 (br s, 2H), 4.22 (m, 1H), 2.84 (dd, J=7.6 18 Hz, 1H), 2.45 (dd, J=2.8 17.6 Hz, 1H).

A solution of compound e (30 g, 127 mmol) and Me₂NH (excess) in 200 ml of dioxane was stirred at 0° C. for 24 hours and concentrated, EtOAc (500 ml) was added and washed with brine, dried over Na₂SO₄ and concentrated. The resulting oil of e was prepared for the next step without further purification (32 g, 90%). MS (ESI) m/e (M+H⁺): 281; ¹H-NMR (CDCl₃, 400 MHz): δ 7.35-7.27 (m, 5H), 5.89 (m, 1H), 5.09 (s, 2H), 3.97 (m, 1H), 3.78-3.67 (m, 2H), 2.77-2.62 (m, 2H).

To a solution of compound e (20 g, 71 mmol) and triethylamine (7.9 g, 78 mmol) in dry DCM (300 mL) was added methanesulfonyl chloride (8.9 g, 78 mmol) (diluted 1:1 in DCM) with the temperature maintained <10° C. After the addition, the reaction was stirred for 1 hour at 0° C. Upon completion, the reaction was quenched with water (50 mL). The aqueous layer was cut and the organic layer was dried over Na₂SO₄. The solvent was removed under vacuum to afford f as a yellow oil, which was used for the next step without purification. MS (ESI) m/e (M+H⁺):359.

To a solution of PhSH (8.6 g, 78 mmol) in dry THF (300 mL) was added NaH (3.1 g, 78 mmol) in ice-water batches with the temperature maintained <10° C. for 1 hour, then the solution of compound f was added dropwise, the reaction was stirred for another 1.5 hours at rt. Upon completion, the reaction was quenched with water (100 mL) and EtOAc (200 mL). The aqueous layer was cut and the organic layer was washed with brine, dried over Na₂SO₄. The solvent was removed under vacuum and the product g was purified by column (14 g, yield: 48%). MS (ESI) m/e (M+H⁺): 373; ¹H-NMR (CDCl₃, 400 MHz): δ 7.33-7.10 (m, 10H), 6.19 (d, J=8.4 Hz, 1H), 5.01 (s, 2H), 3.97 (m, 1H), 3.70 (d, J=4.4 Hz, 3H), 3.56 (d, J=4.4 Hz, 3H), 3.28 (m, 1H), 3.14 (m, 1H), 2.81 (m, 1H), 2.45 (m, 1H)

A solution of compound g (4 g, 11 mmol) in 30% HBr in acetic acid (40 ml) was stirred for 24 hours at room temperature, concentrated to half its volume, poured into 1M HCl (40 ml). The combined aqueous layers were washed with ether (3×50 mL) and cooled to 0° C., adjusted to 12 with solid KOH, and extracted with CH₂Cl₂. The combined extracts were washed with brine, dried(Na₂SO₄), filtered, and concentrated to provide the desired product h (1.8 g, yield: 72%). MS (ESI) m/e (M+H⁺): 239; ¹H-NMR (CDCl₃, 400 MHz): δ 7.30 (d, J=7.6 Hz, 2H), 7.21 (t, J=7.6 Hz, 2H), 7.30 (t, J=7.6 Hz, 1H), 3.36 (m, 1H), 3.04 (m, 1H), 2.85 (m, 1H), 2.88 (s, 3H), 2.83 (s, 3H), 2.51 (m, 1H), 2.30 (m, 1H).

A solution of compound h (1.8 g, 7.6 mmol) and compound i (1.7 g, 7.6 mmol) in dioxane was treated with Et₃N (1.5 g, 15.2 mmol) heated to reflux overnight, concentrated, and purified by silica gel chromatography eluting with PE:EA= (1:1) to provide the desired product j (2.3 g, yield: 76%). MS (ESI) m/e (M+H⁺): 439; ¹H-NMR (DMSO, 400 MHz): δ 8.74 (d, J=9.6 Hz, 1H), 8.35 (s, 1H), 7.67 (d, J=8.8 Hz, 1H), 7.41-7.04 (m, 7H), 4.36 (m, 1H), 3.36 (d, J=6.4 Hz, 2H), 3.15 (m, 1H), 2.95 (m, 1H), 2.86 (s, 3H), 2.76 (s, 3H), 2.73 (m, 1H).

A solution of compound j (2.5 g, 5.7 mmol) in 100 mL of dry THF was heated to 55° C. And treated dropwise with a solution of 1M borane (25 mL) in THF over a 1 hour period. The resulting reaction mixture was stirred at 55° C. for 18 hours, cooled to 0° C., treated dropwise with methanol, and concentrated. The crude residue was dissolved in methanol, treated with methanolic HCl, and heated to reflux for 24 hours. The mixture was allowed to cool to room temperature, concentrated, diluted with 2M NaOH, and extracted with EtOAc. The combined extracts were washed with 1M NaOH and brine, dried, filtered, concentrated and purified by silica chromatography eluting with CH₂Cl₂:MeOH=(10:1) to provide the desired product, (R)-4-(4-(dimethylamino)-1-(phenylthio)butan-2-ylamino)-3-nitrobenzenesulfonamide (1.2 g, yield: 46%). MS (ESI) m/e (M+H⁺): 425; ¹H-NMR (CDCl₃, 400 MHz): δ9.05 (d, J=9.6 Hz, 1H), 8.67 (s, 1H), 7.72 (d, J=8.8 Hz, 1H), 7.38-7.36 (m, 2H), 7.30-7.21 (m, 3H), 6.72 (d, J=9.6 Hz, 1H), 7.38-7.36 (m, 2H), 4.00 (m, 1H), 3.14 (d, J=6.4 Hz, 2H), 2.49 (m, 1H), 2.32 (m, 1H), 2.05 (m, 1H), 1.84 (m, 1H).

Example 4

4-((R)-3-morpholin-4-yl-1-phenylsulfanylmethyl-propylamino)-3-trifluoromethanesulfonyl-benzene-sulfonamide

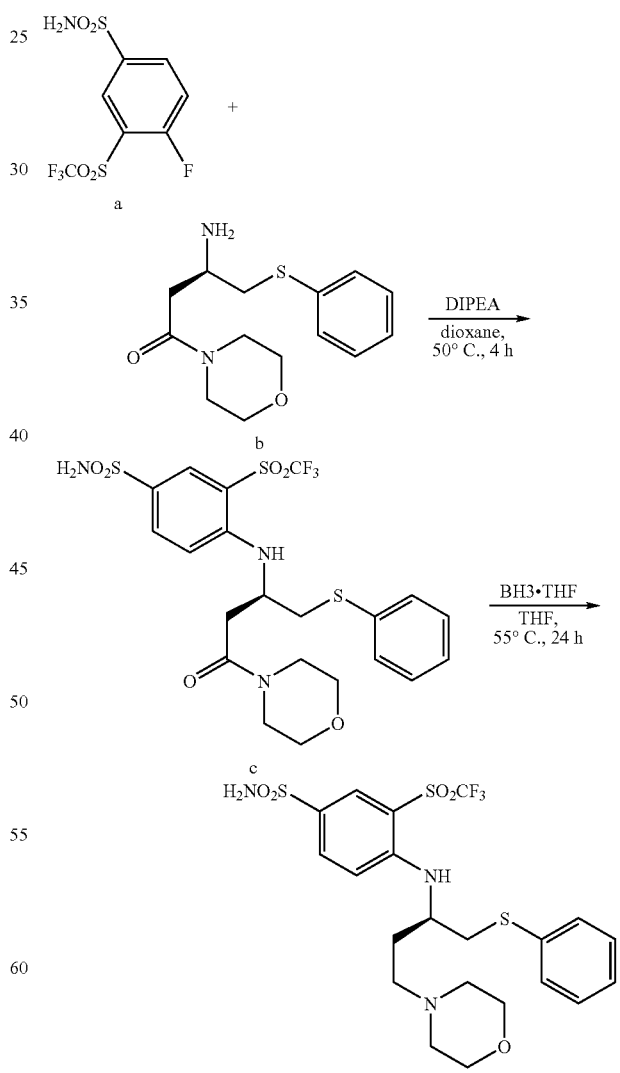

The sulfonamide a (1.63 mmol), amine b (1.63 mmol) and diisopropylethylamine (3.26 mmol) in dioxane was stirred at 50° C. for 4 h. The mixture was treated 10% sodium hydrogen carbonate solution (30 ml) and the aqueous solution was then extracted with ethyl acetate (2×20 ml). The organic layer was dried (MgSO$_4$) and concentrated in vacuo. The resulting residue was applied to silica chromatography gradient eluting with 100% dichloromethane to 5% methanol/dichloromethane to yield 4-((R)-3-morpholin-4-yl-3-oxo-1-phenylsulfanylmethyl-propylamino)-3-trifluoromethanesulfonyl-benzenesulfonamide c as a white solid (77%). $^1$H NMR (300 MHz, DMSO) δ 7.97 (1H, d, J 2.2 Hz), 7.83 (1H, dd, J 9.2 and 2.2 Hz), 7.39-7.27 (7H, m, ArH), 7.21 (1H, tt, J 6.8 and 1.65 Hz), 7.00 (1H, bd, J 9.5 Hz), 4.38-4.25 (1H, m), 3.40-3.27 (2H, m), 3.50-3.37 (10H, m), 2.94 (1H, dd, J 16.8 and 5.8 Hz), 2.71 (1H, dd, J 16.8 and 5.1 Hz). LCMS-rt 7.17, M+H 568.

Borane tetrahydrofuran complex (4.21 mmol) was added dropwise over 2 h to the amide intermediate c (1.24 mmol) in tetrahydrofuran (10 ml) at room temperature under a nitrogen atmosphere. The solution was then stirred at 55° C. for 24 h. The solution was cooled to 0° C. and treated with methanol (2 ml). To this mixture was added concentrated hydrochloric acid (0.5 ml) and the solution heated at 65° C. for 10 h. The solution was then concentrated in vacuo and poured into a 2 N sodium hydroxide solution (10 ml). The aqueous layer was then extracted with ethyl acetate (2×10 ml), the organic layer was dried (MgSO$_4$) and concentrated in vacuo. The resulting residue was applied to silica chromatography gradient eluting with 100% dichloromethane to 10% methanol/dichloromethane to yield intermediate 4-((R)-3-morpholin-4-yl-1-phenylsulfanylmethyl-propylamino)-3-trifluoromethane-sulfonyl-benzenesulfonamide, 4-((R)-3-morpholin-4-yl-1-phenylsulfanylmethyl-propylamino)-3-trifluoromethanesulfonyl-benzenesulfonamide as a white solid (76%). $^1$H NMR (300 MHz, DMSO) δ 7.97 (1H, d, J 2.2 Hz), 7.83 (1H, dd, J 9.2 and 2.3 Hz), 7.35-7.26 (6H, m, ArH), 7.20 (1H, tt, J 7.0 and 1.8 Hz), 7.04 (1H, d, J 9.6 Hz), 6.89 (1H, bd, J 9.1 Hz), 4.12-4.02 (1H, m), 3.49 (4H, bs), 3.37-3.22 (2H, m), 2.33-2.14 (6H, m), 1.94-1.88 (1H, m), 1.76-1.70 (1H, m). LCMS-rt-5.69, M+H 554.

Example 5

4-((R)-3-Dimethylamino-1-phenylsulfanyl-methyl-propylamino)-3-trifluoromethanesulfonyl-benzenesulfonamide

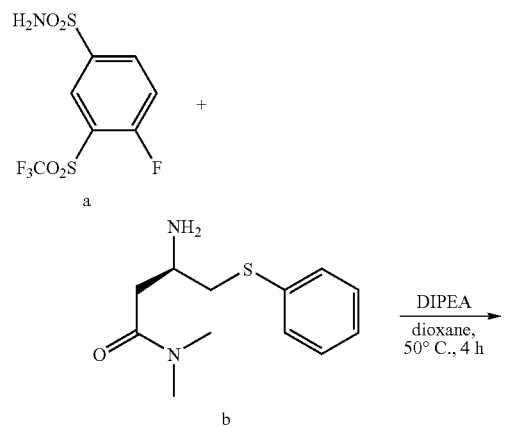

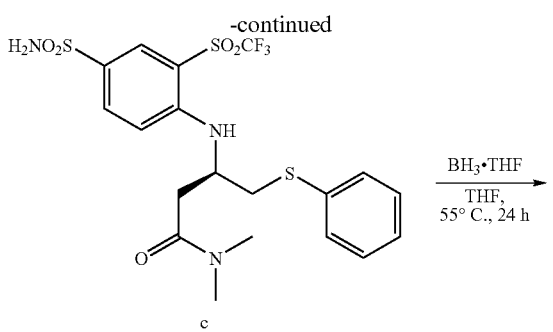

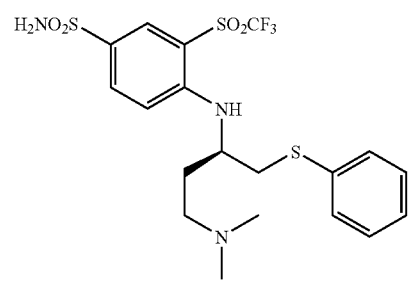

The sulfonamide a (1.63 mmol), amine b (1.63 mmol) and diisopropylethylamine (3.26 mmol) in dioxane was stirred at 50° C. for 4 h. The mixture was treated 10% sodium hydrogen carbonate solution (30 ml) and the aqueous solution was then extracted with ethyl acetate (2×20 ml). The organic layer was dried (MgSO$_4$) and concentrated in vacuo. The resulting residue was applied to silica chromatography gradient eluting with 100% dichloromethane to 5% methanol/dichloromethane to yield intermediate c (R)—N,N-dimethyl-4-phenylsulfanyl-3-(4-sulfamoyl-2-trifluoromethane-sulfonyl-1-phenylamino)-butyramide as a white foam (84%). $^1$H NMR (300 MHz, DMSO) δ 7.97 (1H, d, J 2.2 Hz), 7.83 (1H, dd, J 9.2 and 2.2 Hz), 7.47 (1H, bd, J 8.7 Hz), 7.37-7.30 (6H, m, ArH), 7.21 (1H, tt, J 6.8 and 1.65 Hz), 6.99 (1H, bd, J 9.5 Hz), 4.38-4.25 (1H, m), 3.40-3.27 (2H, m), 2.91 (1H, dd, J 17.2 and 5.6 Hz), 2.86 (3H, s), 2.76 (3H, s), 2.68 (1H, dd, J 16.7 and 5.0 Hz). LCMS-rt-7.24, M+H 526.

Borane tetrahydrofuran complex (4.21 mmol), was added dropwise over 2 h to the intermediate c (1.24 mmol) in tetrahydrofuran (10 ml) at room temperature under a nitrogen atmosphere. The solution was then stirred at 55° C. for 24 h. The solution was cooled to 0° C. and treated with methanol (2 ml). To this mixture was added concentrated hydrochloric acid (0.5 ml) and the solution heated at 65° C. for 10 h. The solution was then concentrated in vacuo and poured into a 2 N sodium hydroxide solution (10 ml). The aqueous was then extracted with ethyl acetate (2×10 ml), the organic layer was dried (MgSO$_4$) and concentrated in vacuo. The resulting residue was applied to silica chromatography gradient eluting with 100% dichloromethane to 10% methanol/dichloromethane to yield 4-((R)-3-dimethylamino-1-phenylsulfanyl-methyl-propylamino)-3-trifluoromethanesulfonyl-benzenesulfonamide as a colourless oil (67%). $^1$H NMR (300 MHz, DMSO) δ 7.97 (1H, d, J 2.2 Hz), 7.81 (1H, dd, J 9.3 and 2.2 Hz), 7.40-7.26 (7H, m, ArH), 7.21 (1H, tt, J 6.8 and 1.65 Hz), 6.97 (1H, bd, J 9.5 Hz), 4.07-4.00 (1H, m), 3.32 (1H, dd, J 13.8 and 6.1 Hz), 3.22 (1H, dd, J 13.8 and 6.4 Hz), 2.42-2.33

(1H, m), 2.19-2.07 (1H, m), 1.92-1.85 (1H, m), 1.77-1.70 (1H, m). LCMS-rt-5.68, M+H 512.

Example 6

7-(piperazin-1-yl)quinazolin-4-ol

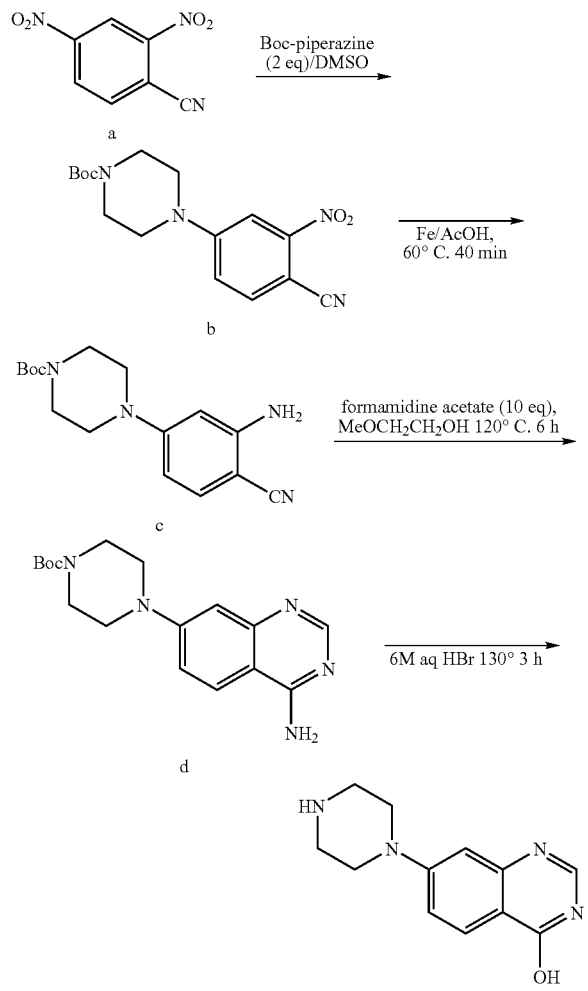

2,4-dinitrobenzonitrile (10 g) and Boc-piperazine (20 g, ca 2 eq) in DMSO (60 ml) was stirred for 3 days at room temperature. The dark brown reaction mixture was then partitioned between ethyl acetate (ca 400 ml) and water (ca 2×100 mL) [note—warming was sometime needed in order to prevent product from crystallizing out of organic layer]. The separated and dried organic layer was concentrated and the residue triturated with ether and filtered to give intermediate b (1st crop 8 g, 47% yield,) as a deep yellow powder. A $2^{nd}$ crop was obtained from the ethereal ethyl acetate supernatant on standing after some evaporation had taken place ($2^{nd}$ crop. 1.7 g, 10%).

Intermediate b (3 g) was reduced to the aniline c using iron powder (2 g) in acetic acid (20 ml) at 60 deg. with rapid stirring. The reaction mixture was diluted with ethyl acetate (ca 60 ml), filtered twice through celite, and the acetic acid removed with a base wash using ca 6M aq. NaOH. The washed organic layer was separated and dried and concentrated to give intermediate c (52-72% yield) as a pale yellow powder.

Intermediate c (1.5 g) in MeOCH$_2$CH$_2$OH (10 ml) at 120 deg. was treated portionwise (4×2.5 eq over the period of an hour) with formamidine acetate and the whole heated for a further 6 hours, during which time the reaction mixture became heterogenous due to product formation. After standing overnight at room temperature, the reaction mixture was shaken with ether (ca 40 mL) and filtered and the filtercake washed further with ether, then slurried with water (ca 40 ml) and re-filtered to give intermediate d as a colourless powder (ca 1.1 g, 69%). On standing, the filtrate after evaporation of the organic layer gave a further crop of crude product (ca 22%).

Intermediate d (4 mmol) was then added carefully with rapid stirring [note—vigorous effervescence occurred] to ca 6M aq. HBr (ca 5-6 mL) to initially remove the Boc group giving the intermediate V. Further stirring and heating at 130° C. in a capped vessel for 3 h gave the hydrolysed product 7-(piperazin-1-yl)quinazolin-4-ol dihydrobromide as colourless needles (97%) after the hot reaction mixture was added to hot methanol (ca 50 mL) and the whole allowed to cool overnight and filtered [note—cooling too rapidly led to an intractable gel]. M$^+$ 231.

Example 7

2-bromomethyl-4'-chloro-biphenyl

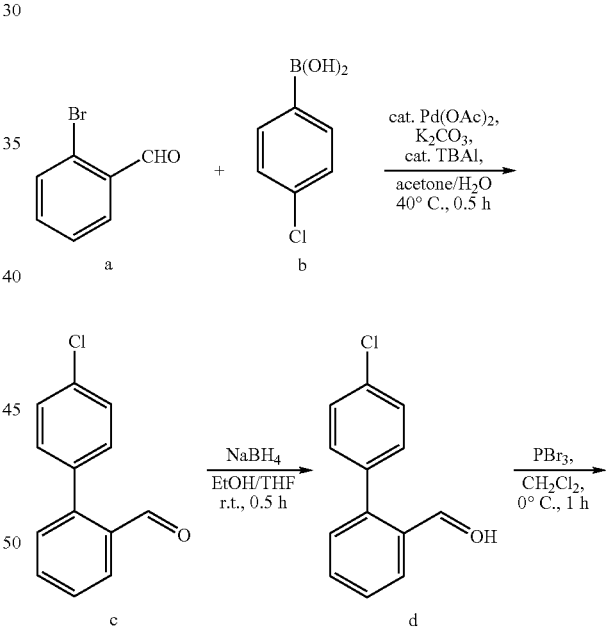

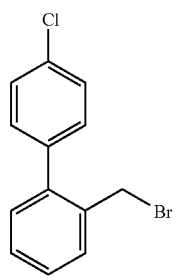

2-Bromobenzaldehyde a (19 mmol), 4-chlorophenyl boronic acid b (19 mmol), tetrabutylammonium iodide (0.19 mmol), potassium carbonate (57 mmol) and palladium acetate (0.12 mmol) in mixture of acetone/water (25 ml/25 ml) was stirred at 40° C. for 30 mins. The mixture was partitioned between ethyl acetate and water and the layers were separated. The organic layer was dried (MgSO$_4$) and concentrated in vacuo. The resulting residue was applied to silica chromatography gradient eluting with 100% petroleum ether to 5% ethyl acetate/petroleum ether to yield intermediate c 4'-chloro-biphenyl-2-carbaldehyde as a colourless oil (76%). $^1$H NMR (300 MHz, CDCl$_3$) δ 9.96 (1H, s), 8.02 (1H, dd, J 7.8 and 1.0 Hz), 7.64-7.30 (7H, m, ArH).

Sodium borohydride (11.5 mmol) was added to a mixture of the aldehyde (2.3 mmol) in a mixture of tetrahydrofuran and ethanol (7.5 ml/7.5 ml) at room temperature. The mixture was stirred for 30 mins and was then quenched by addition of cold water. The pH was adjusted to pH 5-6 and the solution stirred for 15 mins. Diethyl ether (20 ml) was added to the solution and layers were then separated. The aqueous solution was extracted once more with diethyl ether (20 ml). The combined organic layers were dried (MgSO$_4$) and concentrated in vacuo to yield intermediate d 4'-chloro-biphenyl-2-yl)-methanol as a colourless oil (95%). The compound was of sufficient purity to be used in the next step without further purification. $^1$H NMR (300 MHz, DMSO) δ 7.56-7.18 (8H, m, ArH) 5.1 (1H, bs, OH) and 4.36 (2H, s, ArCH$_2$).

Phosphorous tribromide (4.6 mmol) in dichloromethane (10 ml) was added slowly to a solution of the alcohol d (4.6 mmol) in dry dichloromethane (40 ml) at 0° C. The solution was allowed to stir for 1 h at 0° C. and was then quenched by addition of cold water. The layers were separated and then aqueous was extracted with dichloromethane (20 ml). The combined organic layers were dried (MgSO$_4$) and concentrated in vacuo. Further drying yielded intermediate 2-bromomethyl-4'-chloro-biphenyl as a white solid (80%). The compound was of sufficient purity to be used in the next step without further purification. $^1$H NMR (300 MHz, CDCl$_3$) δ 7.56-7.23 (8H, m, ArH) and 4.44 (2H, s, ArCH$_2$).

Example 8

1-(2-(bromomethyl)-4,4-dimethylcyclohex-1-enyl)-4-chlorobenzene

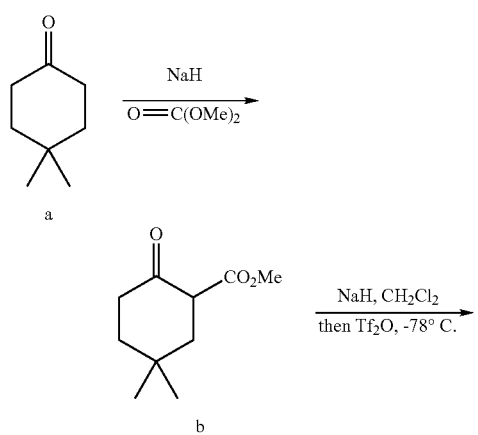

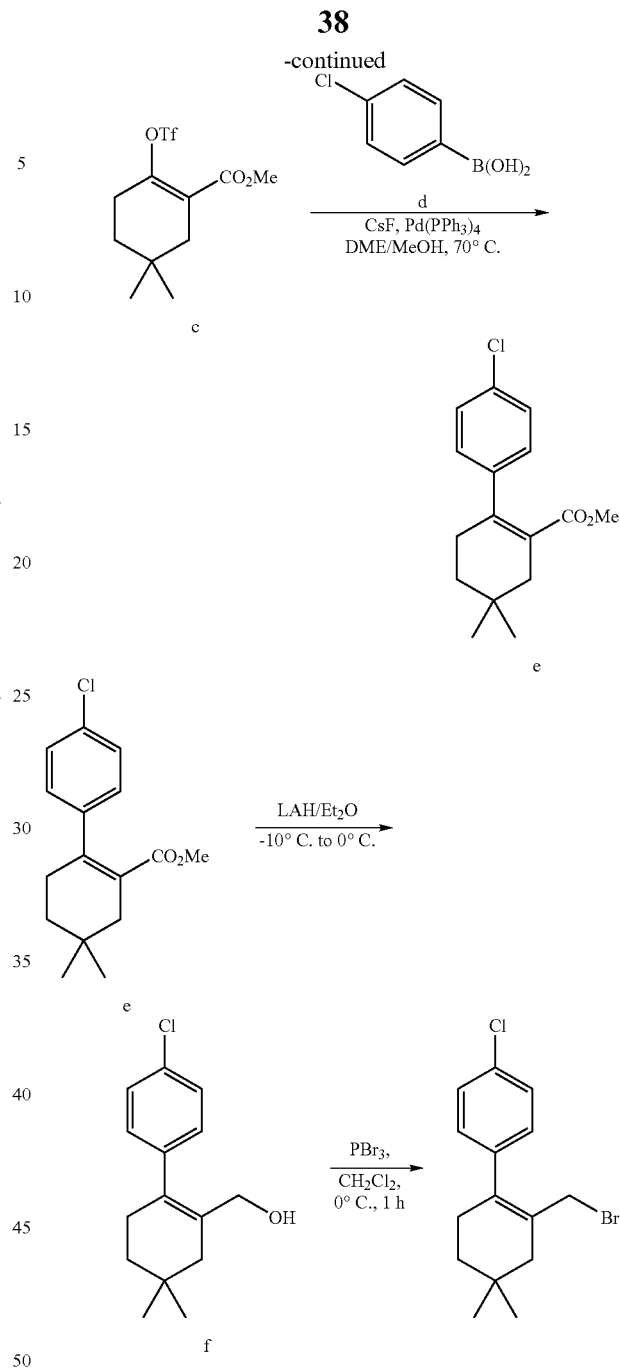

To a solution of 21 g of dimethyl carbonate (0.23 mol) in dry THF (400 ml) was added sodium hydride (9.6 g, 0.24 mol) by portion at 0° C. The resulting mixture was stirred at 0° C. for 30 min and then was added a solution of 10 g of compound a (79 mmol) in THF (100 ml) dropwise over 30 min. The resultant mixture was heated to 60° C.-80° C. for 3 h before cooled to room temperature. The reaction mixture was poured into saturated NaHCO$_3$ solution and extracted with ether. The organic layer was washed with water, brine, dried over Na$_2$SO$_4$ and concentrated to give 25 g of intermediate b methyl 5,5-dimethyl-2-oxocyclohexanecarboxylate (yield: 84%). MS (ESI) m/e (M+H$^+$): 185.

To a solution of b (10 g, 54 mmol) in dry DCM (100 ml) was added sodium hydride (6.6 g, 0.16 mol) by portion at 0° C. The resulting mixture was stirred at 0° C. for 30 min and then was cooled down to −78° C. 46.6 g of trifluoromethanesulfonic anhydride was added to the slurry dropwise over 1 h. The resultant mixture was warmed to r. t. and stirred overnight. The reaction mixture was poured into saturated NaHCO₃ solution and extracted with DCM. The organic layer was washed with water, brine, dried over Na₂SO₄ and concentrated to give the crude product, which was purified by column to afford 9.5 g of intermediate c methyl 5,5-dimethyl-2-(trifluoromethylsulfonyloxy)cyclohex-1-ene-carboxylate (yield: 55%). MS (ESI) m/e (M+H⁺): 317.

A mixture of compound c (5.1 g, 16 mmol), compound d (3.0 g, 19 mmol), cesium fluoride (6.1 g, 40 mmol) and tetrakis(triphenylphosphine)palladium(0) (0.8 mmol) in 2:1 DME/methanol (100 ml) was heated to 70° C. under N₂ atmosphere overnight. The mixture was filtered through celite and concentrated to give crude product, which was purified by column to afford 4 g of intermediate e methyl 2-(4-chlorophenyl)-5,5-dimethylcyclohex-1-enecarboxylate (yield: 89%). MS (ESI) m/e (M+H⁺): 279.

To a suspension of LiAlH₄ (0.95 g, 25 mmol) in ether (100 ml) was added intermediate e (2.79 g, 10 mmol) at −10° C. over 30 min. The resultant mixture was stirred for 1 h 30 min at −10° C.~0° C. Then the reaction mixture was quenched with 1 ml water and 1 ml 10% NaOH aqueous solution at 0° C. The resulting mixture was filtered and the filtrate was diluted with ether, then the ether layer wash washed with water, brine, and dried over anhydrous Na₂SO₄ and concentrated to afford 2.3 g of intermediate f (2-(4-chlorophenyl)-5,5-dimethylcyclohex-1-enyl)methanol (yield: 95%). MS (ESI) m/e (M+H⁺): 251/233. ¹H-NMR (DMSO, 400 MHz): δ 7.35 (d, J=8.4 Hz, 2H), 7.20 (d, J=8.4 Hz, 2H), 4.52 (t, J=5.2 Hz, 1H), 3.67 (d, J=4.8 Hz, 1H), 2.21 (t, J=6.0 Hz, 1H), 1.92 (s, 2H), 1.40 (t, J=6.4 Hz, 2H), 0.94 (s, 6H), Phosphorous tribromide (4.6 mmol) in dichloromethane (10 ml) was added slowly to a solution of the intermediate f (4.6 mmol) in dichloromethane (40 ml) at 0° C. The solution was allowed to stir for 1 h at 0° C. and was then quenched by addition of cold water. The layers were separated and then the aqueous was extracted with dichloromethane (20 ml). The combined organic layers were dried (MgSO₄) and concentrated in vacuo to afford 1-(2-bromomethyl-4,4-dimethyl-cyclohex-1-enyl)-4-chloro-benzene as a colourless oil (95%). The compound was of sufficient purity to be used in the next step without further purification. ¹H NMR (300 MHz, CDCl₃) δ 7.26 (4H, q, J 17.2 Hz), 3.83 (2H, s), 2.31-2.27 (2H, m), 2.09 (3H, t, J 2.1 Hz), 1.49 (2H, t, J 6.5 Hz) and 1.01 (6H, s).

Example 9

4-chloro-7-[4-(4'-chloro-biphenyl-2-ylmethyl)-piperazin-1-yl]-quinazoline

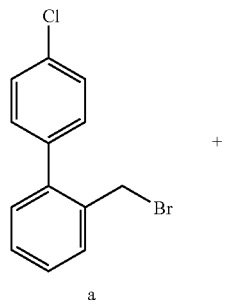

+

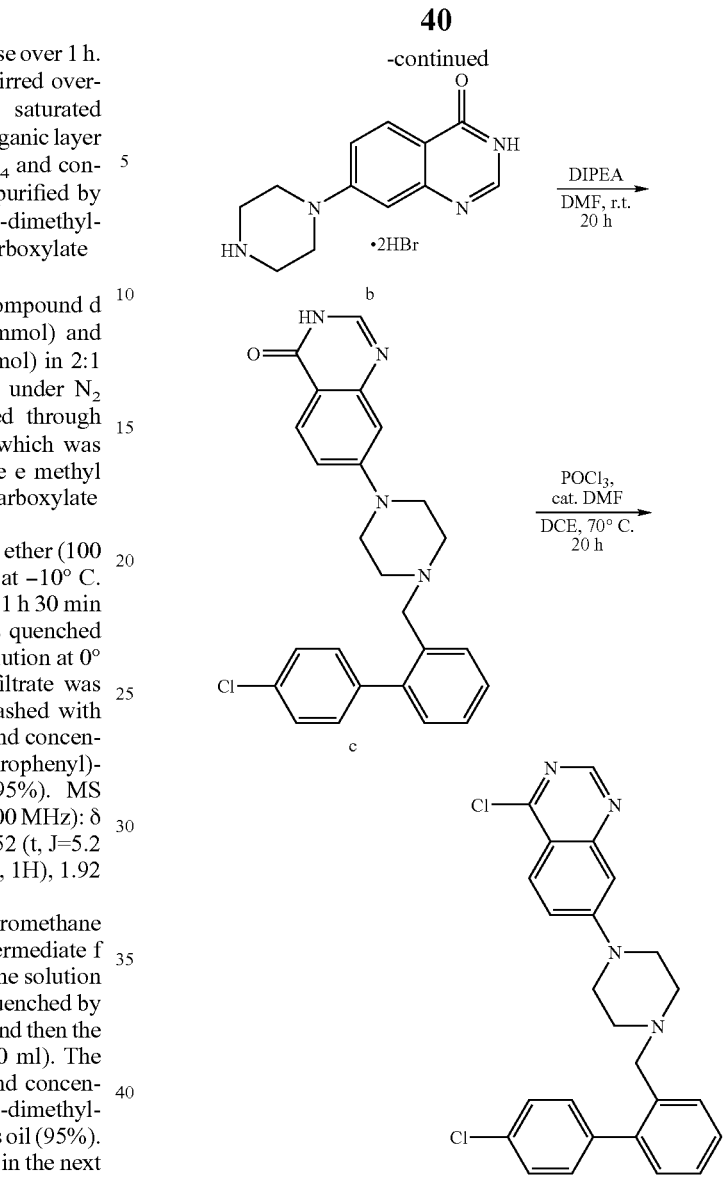

Diisopropylethylamine (2.55 mmol) was added to a stirred solution of the quinazolinone b (1.28 mmol) in N,N-dimethylformamide (10 ml). To this solution the bromide intermediate a (1.28 mmol) in N,N-dimethylformamide (4 ml) was added dropwise over 30 mins. The solution was allowed to stir at room temperature for 20 h. A solution of 10% sodium hydrogencarbonate (50 ml) was added to the stirred solution. The resulting precipitate was filtered off and dried in a vacuum oven to yield intermediate c 7-[4-(4'-Chloro-biphenyl-2-ylmethyl)-piperazin-1-yl]-quinazolin-4-ol as a white solid (80%). The compound was of sufficient purity to be used in the next step without further purification. ¹H NMR (300 MHz, DMSO) δ 7.92 (1H, s), 7.86 (1H, d, J 9.0 Hz) 7.52-7.34 (7H, m), 7.23 (1H, dd, J 6.9 and 1.9 Hz), 7.11 (1H, dd, J 9.0 and 2.2 Hz), 6.88 (1H, d, J 2.3 Hz), 3.38 (2H, s), 3.25 (4H, bs) and 2.41 (4H, bs). LCMS-r.t. 5.77, M+H 431.

A solution of phosphorous chloride (0.5 ml) and N,N-dimethylformamide (0.058 mmol) in 1,2-dichloroethane (2 ml) was added dropwise over 15 mins to a stirred solution of the quinazolinone c (1.16 mmol) in 1,2-dichloroethane (30 ml) at 70° C. under an atmosphere of nitrogen. Additional phosphorous chloride was added in increments (1 ml) of 15 mins over the next hour. The solution was allowed to stir at 70° C. for 20 h. The solution was then concentrated in vacuo to dryness and then diluted with a solution of 10% sodium hydrogencarbonate (40 ml) and dichloromethane (40 ml). The layers were separated, the organic layer was dried (MgSO₄) and concentrated in vacuo. The resulting residue was then applied to alumina column chromatography gradient eluting from 100% dichloromethane to 0.5% methanol/dichloromethane to afford 4-chloro-7-[4-(4'-chloro-biphenyl-2-ylmethyl)-piperazin-1-yl]-quinazoline as a yellow foam (55%). ¹H NMR (300 MHz, CDCl₃) δ 8.80 (1H, s), 8.02 (1H, d, J 9.4 Hz) 7.37-7.24 (7H, m), 7.12 (1H, d, J 2.5 Hz), 3.45 (6H, bs), 2.55 (4H, s). LCMS-r.t. 3.67, M+H 449.

Example 10

4-chloro-7-(4-((2-(4-chlorophenyl)-5,5-dimethylcyclohex-1-enyl)methyl)piperazin-1-yl)quinazoline

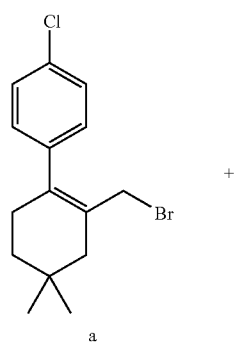

a

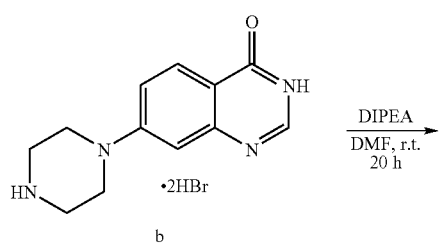

b

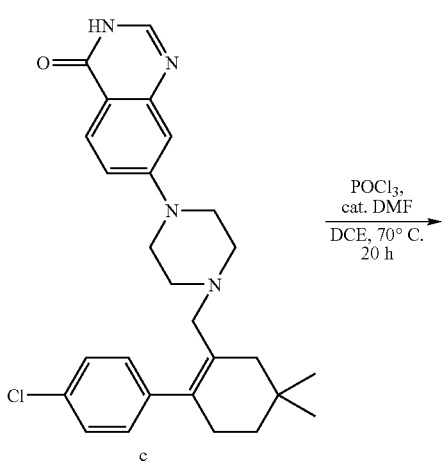

c

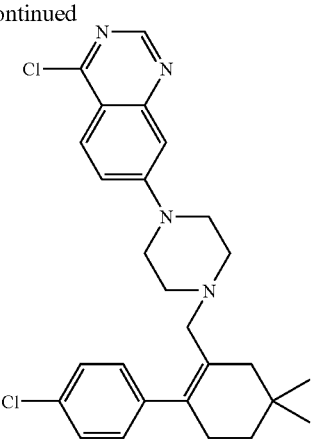

Diisopropylethylamine (2.55 mmol) was added to a stirred solution of the quinazolinone b (1.28 mmol) in N,N-dimethylformamide (10 ml). To this solution the bromide a (1.28 mmol) in N,N-dimethylformamide (4 ml) was added dropwise over 30 mins. The solution was allowed to stir at room temperature for 20 h. A solution of 10% sodium hydrogencarbonate (50 ml) was added to the stirred solution. The resulting precipitate was filtered off and dried in a vacuum oven to yield intermediate c as a white solid (84%). The compound was of sufficient purity to be used in the next step without further purification. ¹H NMR (300 MHz, DMSO) δ 7.92 (1H, s), 7.83 (1H, d, J 9.0 Hz) 7.36 (2H, d, J 6.5 Hz), 7.15 (2H, d, J 6.5 Hz), 7.06 (1H, dd, J 9.0 and 2.4 Hz), 6.82 (1H, d, J 2.3 Hz), 3.25 (4H, bs), 2.74 (2H, bs), 2.27-2.21 (6H, m), 1.98 (2H, s), 1.42 (2H, t, J 6.4 Hz) and 0.96 (6H, s). LCMS-r.t. 5.95, M+H 463.

A solution of phosphorous chloride (0.5 ml) and N,N-dimethylformamide (0.058 mmol) in 1,2-dichloroethane (2 ml) was added dropwise over 15 mins to a stirred solution of the quinazolinone c (1.16 mmol) in 1,2-dichloroethane (30 ml) at 70° C. under an atmosphere of nitrogen. Additional phosphorous chloride was added in increments (1 ml) of 15 mins over the next hour. The solution was allowed to stir at 70° C. for 20 h. The solution was then concentrated in vacuo to dryness and then diluted with a solution of 10% sodium hydrogencarbonate (40 ml) and dichloromethane (40 ml). The layers were separated, the organic layer was dried (MgSO₄) and concentrated in vacuo. The resulting residue was then applied to alumina column chromatography gradient eluting from 100% dichloromethane to 0.5% methanol/dichloromethane to afford 4-chloro-7-(4-((2-(4-chlorophenyl)-5,5-dimethylcyclohex-1-enyl)methyl)piperazin-1-yl)quinazoline as a yellow foam (58%). LCMS-r.t. 6.41, M+H 463.

Example 11
Compound 1

N-{7-[4-(4'-Chloro-biphenyl-2-ylmethyl)-piperazin-1-yl]-quinazolin-4-yl}-4-((R)-3-dimethylamino-1-phenylsulfanylmethyl-propylamino)-3-nitro-benzenesulfonamide

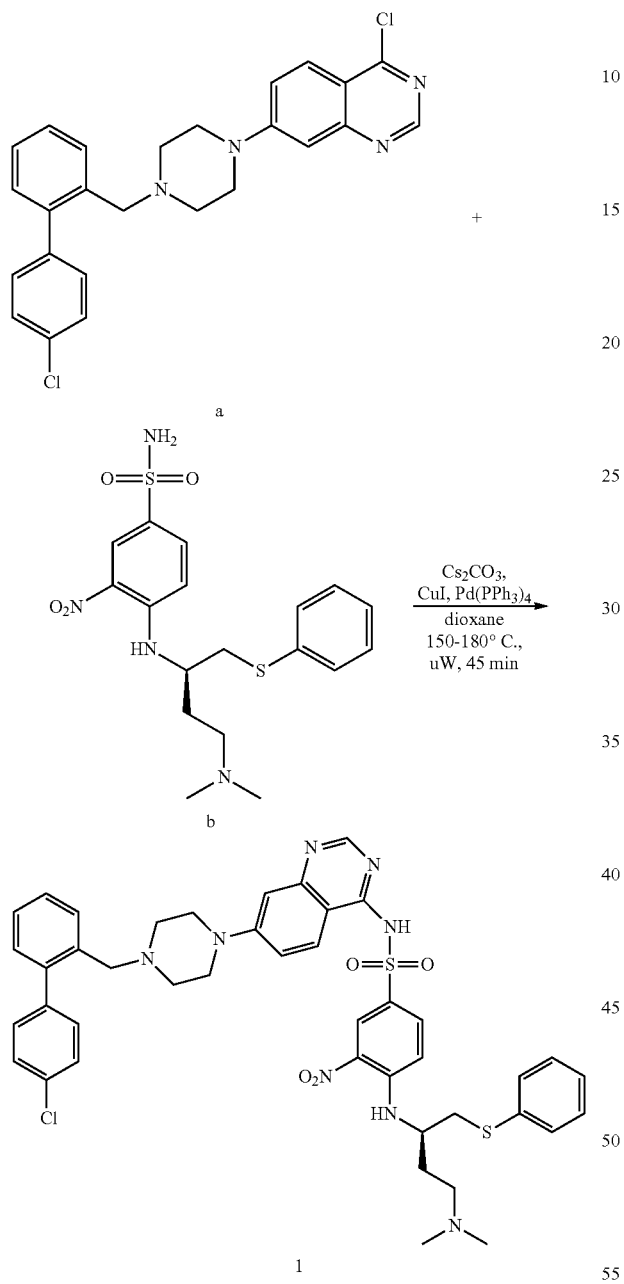

A solution of the chloroquinazoline a (0.22 mmol), the sulfonamide b (0.22 mmol), cesium carbonate (0.31 mmol), palladium tetrakis(triphenylphosphine) (0.015 mmol), copper iodide (0.03 mmol) in dioxane (4 ml) was degassed for 5 mins before being subject to microwave irradiation (300 W, 150-180° C., CEM Discover Labmate) for 45 mins. The mixture was filtered washing with ethyl acetate and then washed with solution of 10% sodium hydrogencarbonate (10 ml). The organic layer was dried (MgSO$_4$) and concentrated in vacuo to give a crude residue (90%). This residue was then subject to preparative reverse phase HPLC for purification of final compound 1. $^1$H NMR (300 MHz, CDCl$_3$) δ. LCMS-r.t. 5.77, M+H 837.

Compounds 2-8 were prepared according to analagous procedures:

Compound 2

N-{7-[4-(4'-Chloro-biphenyl-2-ylmethyl)-piperazin-1-yl]-quinazolin-4-yl}-4-((R)-3-dimethylamino-1-phenylsulfanylmethyl-propylamino)-3-trifluoromethanesulfonyl-benzenesulfonamide $^1$H NMR (300 MHz, CDCl$_3$) δ
LCMS-r.t. 5.98, M+H 924.

Compound 3

N-{7-[4-(4'-Chloro-biphenyl-2-ylmethyl)-piperazin-1-yl]-quinazolin-4-yl}-4-((R)-3-morpholin-4-yl-1-phenylsulfanylmethyl-propylamino)-3-nitro-benzenesulfonamide $^1$H NMR (300 MHz, CDCl$_3$) δ
LCMS-r.t. 5.78, M+H 879.

Compound 4

N-{7-[4-(4'-Chloro-biphenyl-2-ylmethyl)-piperazin-1-yl]-quinazolin-4-yl}-4-((R)-3-morpholin-4-yl-1-phenylsulfanylmethyl-propylamino)-3-trifluoromethanesulfonyl-benzenesulfonamide $^1$H NMR (300 MHz, CDCl$_3$) δ
LCMS-r.t. 6.00, M+H 966.

Compound 5

N-(7-{4-[2-(4-Chloro-phenyl)-5,5-dimethyl-cyclohex-1-enylmethyl]-piperazin-1-yl}-quinazolin-4-yl)-4-((R)-3-dimethylamino-1-phenylsulfanylmethyl-propylamino)-3-nitro-benzenesulfonamide $^1$H NMR (300 MHz, CDCl$_3$) δ
LCMS-r.t. 5.97, M+H 869.

Compound 6

N-(7-{4-[2-(4-Chloro-phenyl)-5,5-dimethyl-cyclohex-1-enylmethyl]-piperazin-1-yl}-quinazolin-4-yl)-4-((R)-3-dimethylamino-1-phenylsulfanylmethyl-propylamino)-3-trifluoromethanesulfonyl-benzenesulfonamide $^1$H NMR (300 MHz, CDCl$_3$) δ
LCMS-r.t. 6.11, M+H 956.

Compound 7

N-(7-{4-[2-(4-Chloro-phenyl)-5,5-dimethyl-cyclohex-1-enylmethyl]-piperazin-1-yl}-quinazolin-4-yl)-4-((R)-3-morpholin-4-yl-1-phenylsulfanylmethyl-propylamino)-3-nitro-benzenesulfonamide $^1$H NMR (300 MHz, CDCl$_3$) δ
LCMS-r.t. 5.99, M+H 911.

Compound 8

N-(7-{4-[2-(4-Chloro-phenyl)-5,5-dimethyl-cyclohex-1-enylmethyl]-piperazin-1-yl}-quinazolin-4-yl)-4-((R)-3-morpholin-4-yl-1-phenylsulfanylmethylpropylamino)-3-trifluoromethanesulfonyl benzenesulfonamide $^1$H NMR (300 MHz, CDCl$_3$) δ
LCMS-r.t. 6.16, M+H 998.

Example 12

Compound 1 (R)—N-(7-(4-((4'-chlorobiphenyl-2-yl)methyl)piperazin-1-yl)quinazolin-4-yl)-4-(4-(dimethylamino)-1-(phenylthio)butan-2-ylamino)-3-nitrobenzenesulfonamide

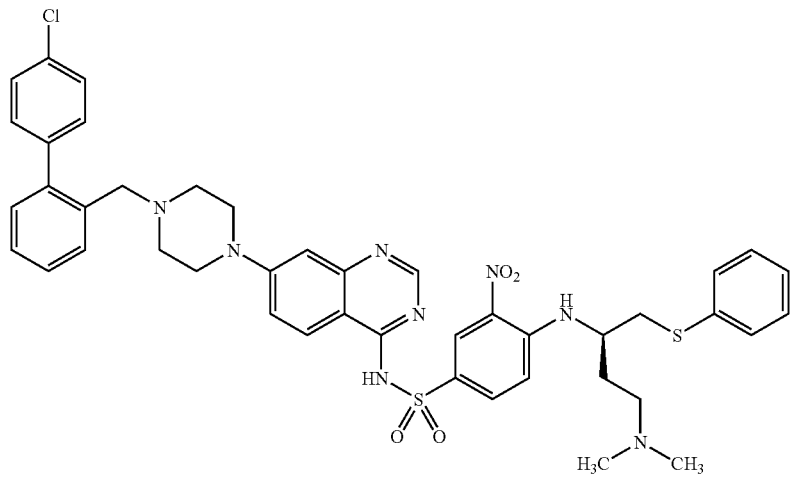

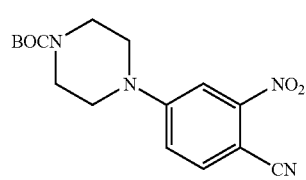

a)

Boc-piperazine (20 mmol) in DMSO (20 mL) was treated with 2,4-dinitrobenzonitrile (10 mmol) and the reaction mixture, which immediately became deep orange/red, was stirred overnight at room temperature. The reaction mixture was partitioned between ethyl acetate and 10% citric acid, the ethyl acetate layer further washed, evaporated and the residue triturated with ether to give a piperizinyl product (yield 33%) as a yellow powder. If contaminated with starting nitrile, crystallisation from ethyl acetate/ether was effective (M+ [ES+]333, $^1$H δ: (ppm, d6-DMSO) 7.82, d ($J_1$ 8.86 Hz), 1H, ArH; 7.66, d ($J_2$, 2.52 Hz), 1H, ArH; 7.28, dd ($J_1$ 8.86 Hz, $J_2$ 2.52 Hz), 1H, ArH; 3.4-3.5, m, 8H, 4×CH$_2$; 1.39, m, 9H, CMe$_3$.

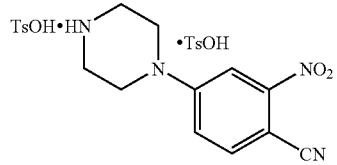

b)

The piperazinyl compound (15 mmol) was deprotected by dissolving in acetonitrile (40 mL) and treating with 5 equivalents of p-toluenesulfonic acid in acetonitrile (20 mL) and standing 2 hours. The product in the form of a bis-tosylate was then filtered off as course prisms (yield 83%). (M+ [ES+] 233; $^1$H δ: (ppm, d6-DMSO) 8.80, bs, 1H, N+H, 7.88, d ($J_1$ 8.82 Hz), 1H, ArH; 7.76, d ($J_2$ 2.58 Hz), 1H, ArH; 7.46, d ($J_1$ 8.07 Hz), 4H, 4×ArH; 7.37, dd ($J_1$ 8.82 Hz, $J_2$ 2.58 Hz), 1H, ArH; 7.09, d ($J_1$ 8.07 Hz), 4H, 4×ArH; 3.6-3.7, m, 4H, 2×CH$_2$; 3.1-3.3, m, 4H, 2×CH$_2$; 2.25, s, 6H, 2×Me.

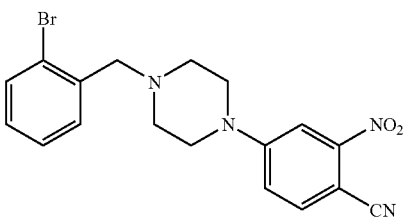

c)

To 4 mmol of this bis-tosylate and 6 mmol of 2-bromobenzylbromide in isopropanol (15 mL) was added triethylamine (14 mmol) and the whole stirred for 3 hours. Methanol was then added (20 mL), the mixture allowed to stand a few minutes, and the aryl bromide product, was filtered off pure as an orange powder (93%). (M+ [ES+] 401, 403; $^1$H δ: (ppm, d6-DMSO) 7.80, d ($J_1$ 8.9 Hz), 1H, ArH; 7.67, d ($J_2$ 2.47 Hz), 1H, ArH; 7.58, d ($J_1$ 7.6 Hz), 1H, ArH; 7.49, d ($J_1$ 7.6 Hz), 1H, ArH; 7.36, dd ($J_1$ 7.6 Hz, $J_1$ 7.6 Hz), 1H, ArH; 7.30, dd ($J_1$ 8.9 Hz, $J_2$ 2.47 Hz); 7.19, dd ($J_2$ 7.6 Hz, $J_1$ 7.6 Hz); 3.58, s, 2H, CH$_2$; 3.4-3.5, m 4H, 2×CH$_2$; 2.5-2.6, m 4H, 2×CH$_2$.

d)

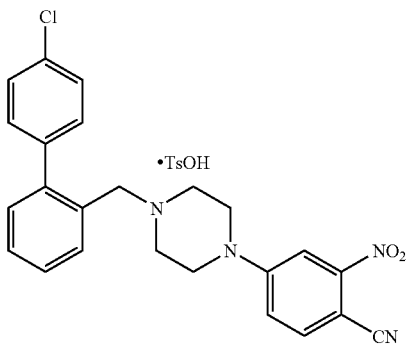

To a mixture of 3.43 mmol of the aryl bromide, 703 mg of p-chlorophenylboronic acid, and 50 mg PdCl$_2$(PPh$_3$)$_2$ stirring in 1:1:1 dimethoxyethane:ethanol:water (20 mL) under nitrogen was added 2M aqueous sodium carbonate solution (2.25 mL) and the solution heated at 90° C. for 4 hours. The reaction mixture was partitioned between ethyl acetate and water, filtered through celite, the organic layer dried, evaporated and the residue treated with 10 mmol of p-toluenesulfonic acid in acetonitrile (20 mL) with ether (40 mL) then added. On standing in the freezer, the nitroarene product precipitated as a yellow powder: yield 1.68 g (81%). (M$^+$ [ES$^+$] 433, 435; $^1$H δ: (ppm, d6-DMSO) 9.57, bs, 1H, N$^+$H; 7.85, d (J$_1$ 8.8 Hz), 1H, ArH; 7.7-7.8, m, 1H, ArH; 7.69, d (J$_2$ 2.52 Hz), 1H, ArH; 7.4-7.6, m, 6H, 6×ArH; 7.2-7.4, m, 4H, 4×ArH; 7.08, d (J$_1$ 7.9 Hz), 2H, 2×ArH; 4.36, m, 2H, CH$_2$; 4.07, m, 2H, CH$_2$; 3.22, m, 4H, 2×CH$_2$; 2.88, m, 2H, CH$_2$; 2.25, 2, 3H, Me.

e)

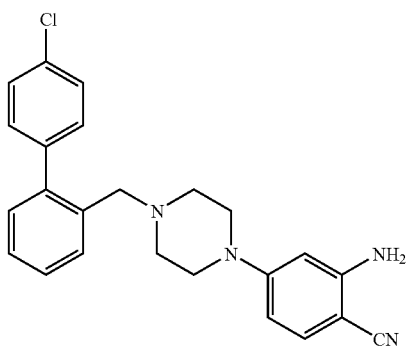

The nitroarene compound (62 mg) and iron powder (50 mg) in glacial acetic acid (0.2 ml) was heated at 908 C. with stirring for 10 minutes, partitioned between ethyl acetate and saturated aqueous sodium bicarbonate solution, the organic layer separated, washed and evaporated to dryness to give the crude aniline, as a brownish residue. This was repeated on a 1.3 g scale. The crude residue was purified by triturating with ether. This gave the aniline product in ca 60% yield, and a further 25% could be recovered from the ethereal supernatant if so desired. (M$^+$ [ES$^+$] 403, 405; $^1$H δ: (ppm, d6-DMSO) 7.1-7.6, m, 9H, 9×ArH; 6.23, d (J$_1$ 9.2 Hz), 1H, ArH; 6.04, s, 1H, ArH; 4.23, bs, 2H, CH$_2$; 3.40, bs, 2H, NH$_2$; 3.19, bs, 4H, 2×CH$_2$; 2.34, bs, 4H, 2×CH$_2$.

f)

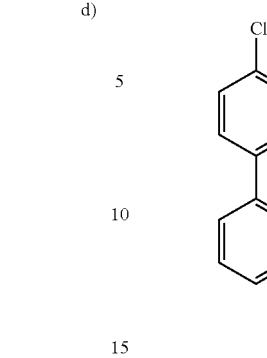

The aniline compound (216 mg) was on-reacted with formamidine acetate (10 eq) in MeOCH$_2$CH$_2$OH (5 mL) at reflux for 3 hours under nitrogen, and the product precipitated from the dark, cooled reaction mixture by the addition of a little water. This was filtered and dried to give the 4-aminoquinazoline compound, as a buff solid that could be recrystallised from aqueous DMSO after neutralisation with aqueous ammonia (198 mg, yield 81%). M$^+$ [ES$^+$] 430, 432. $^1$H δ: (ppm, d6-DMSO) 8.18, s, 1H, ArH (H2); 7.95, d, (J 9.2 Hz), 1H, ArH (H5); 7.47-7.50, m, 1H, ArH; 7.45, bs, 4H, 4×ArH; 7.29-7.36, m, 4H, 2×ArH+NH$_2$; 7.20-7.23, m, 1H, ArH; 7.16, dd (J, 9.2 Hz, J$_2$ 2.4 Hz) 1H, ArH; 6.80, d, (J 2.3 Hz), 1H, ArH; 3.37, s, 2H, CH$_2$; 3.23, m, 4H, 2×CH$_2$ (piperazine); 2.40, m, 4H, 2×CH$_2$ (piperazine).

g)

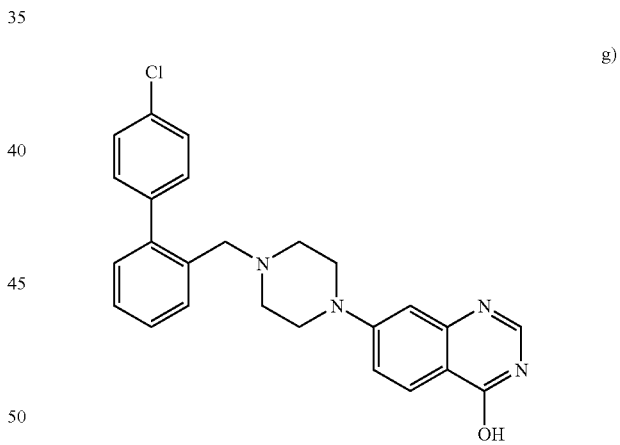

The 4-aminoquinazoline compound (176 mg) was heated at ca 130° C. for 9 hours in glacial acetic acid (2 mL) and concentrated aqueous (25%) hydrochloric acid solution (2 mL) in a small flask fitted with an air condenser. The solvent was removed and the residue recrystallised from aqueous DMSO after neutralisation with minimal aqueous ammonia. This gave the hydrolysed product as a buff powder (87% yield). M$^+$ [ES$^+$] 431, 433. $^1$H δ: (ppm, d6-DMSO) 11.8, bs, 1H, OH; 7.90, s, 1H, ArH (H2); 7.84, d (J 9.0 Hz), 1H, ArH (H5); 7.46-7.51, m, 1H, ArH; 7.44, bs, 4H, 4×ArH; 7.30-7.38, m, 2H, 2×ArH; 7.20-7.23, m, 1H, ArH, 7.09, dd, (J, 9.0 Hz, J$_2$ 2.0 Hz) 1H, ArH; 6.86, d, (J 2.0 Hz) 1H, ArH; 4.44-3.37, bs, 2H, NCH$_2$Ph; 3.27, m, 4H, 2×CH$_2$ (piperazine) 2.38, bm, 4H, 2×CH$_2$, (piperazine).

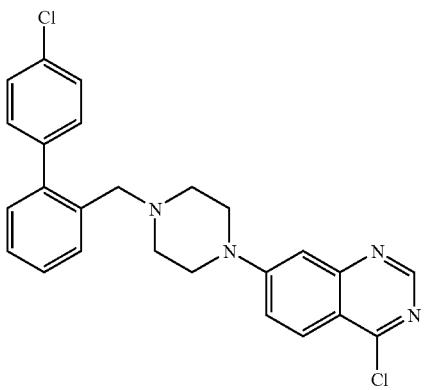

The hydrolysed product was chlorinated by treating 30 mg in 1 mL dry chloroform and 1 mL thionyl chloride with a catalytic amount of DMF (10 uL), refluxing 1 hour, pouring onto ice and extracting product with ethyl acetate, to give the chlorinated product which was on-reacted without characterization.

i) A portion of the chlorinated product from h) (ca 8 mg) was coupled to the sulfonamide (8 mg) prepared in the following example by heating at 85° C. in DMF (0.2 mL) with potassium carbonate (40 mg) overnight. The reaction mixture was partitioned between ethyl acetate (2 mL) and water (2 mL), and the organic layer separated, dried and evaporated to give a yellow residue. This was purified by HPLC to give 2 mg of the compound 2 as a yellow glass, about 80% pure with peak retention time of 3.52 mins and molecular ion peak in ES+ of 837 (major) and 839 (minor).

HPLC Conditions

Solvents:

A: H2O+0.1% formic acid

B: MeCN+0.1% formic acid

C: H2O

D MeCN

Pressure:

Minimum (psi) 0.00

Maximum (psi) 6258.00

Column:Phenomenex Gemini 5u C18 110A; 50×2.00 mm.

Program:

| Time (min) | Flow (mL/min) | A(%) | B(%) | C(%) | D(%) |
|---|---|---|---|---|---|
| 0.00 | 1.000 | 90 | 10 | 0 | 0 |
| 8.00 | 1.000 | 0 | 100 | 0 | 0 |
| 10.00 | 1.000 | 0 | 100 | 0 | 0 |
| 10.10 | 1.000 | 90 | 10 | 0 | 0 |
| 12.00 | 1.000 | 90 | 10 | 0 | 0 |
| 12.10 | 0.000 | 90 | 10 | 0 | 0 |

Example 13

(R)-4-(4-(dimethylamino)-1-(phenylthio)butan-2-ylamino)-3-nitrobenzenesulfonamide for used in example 12

The procedure followed for the preparation of this compound was generally from Wendt et al, with adaptations as follows:

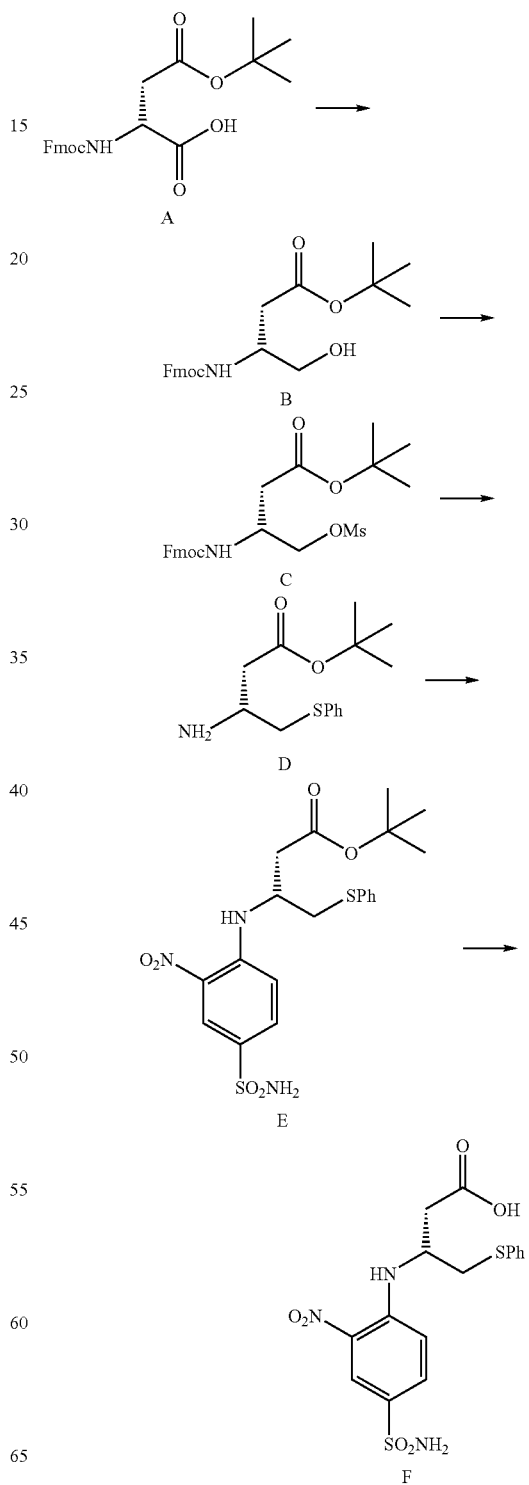

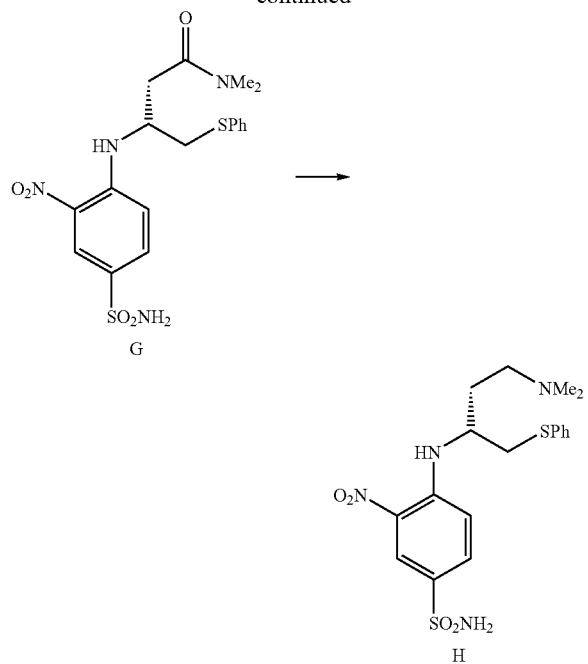

G

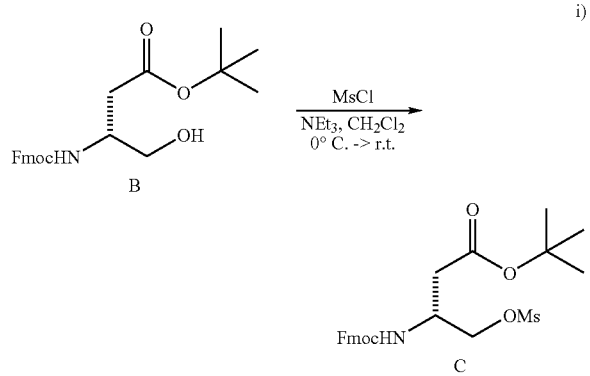

H

Wendt's procedure was followed for preparation of compounds B and E to H. However, compounds C and D were prepared as follows:

i)

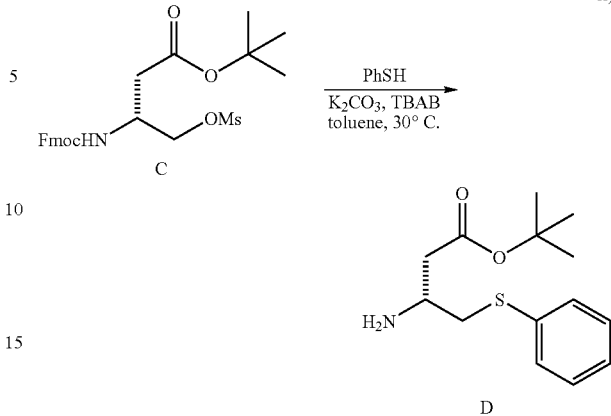

Mesyl chloride (16 μL, 1.2 eq.) was added dropwise to a solution of the purified Fmoc amino alcohol B (68 mg, 0.17 mmol) (purification on silica gel using petroleum ether/ethyl acetate 95:5 to 60:40) in solution with triethylamine (29 μL, 1.2 eq.) in 1 mL of dichloromethane at 0° C. The reaction was left at 0° C. for 1 hour and warmed to room temperature. After that time the TLC (50:50 Pet. Et./AcOEt) indicated that no starting material remained. The reaction was then diluted with dichloromethane and washed with 1M NaHSO$_4$, water and brine. The organic phase was then dried over Na$_2$SO$_4$ and concentrated affording a colourless oil. This oil was dissolved in small amount of dichloromethane and petroleum ether was added until a solid started to precipitate. This mixture was left in the freezer overnight. The solid was collected by filtration and rinsed with petroleum ether (yield 83% of C). NMR (CDCl3, ppm): 7.78 (d, 2H), 7.60 (d, 2H), 7.42 (t, 2H), 7.33 (t, 2H), 5.46 (br. d., 1H), 4.43 (br t, 2H), 4.34 (br s, 2H), 4.24 (br t, 1H), 3.03 (s, 3H), 2.61 (br d, 2H), 1.48 (s, 9H).

ii)

The mesylate C (100 mg, 0.21 mmol), thiophenol (43 μL, 2 eq.), potassium carbonate (58 mg, 2 eq.) and tetrabutylammonium bromide (3 mg) were heated at 30° C. in toluene for a total of 87 hours. The crude reaction was poured directly on top of a column and purified by flash chromatography on silica gel: 100% toluene then dichloromethane 100%, then Ethylacetate/Pet. Et. 60:40 to 70:30 (m=43 mg, 77%) of D).

MS: 269 (M+H). NMR (CDCl$_3$, ppm): 7.41-7.38 (m, 2H), 7.32-7.27 (m, 2H), 7.21 (tt, 1H), 3.38-3.30 (m, A$_1$B$_1$A$_2$B$_2$X, 1H), 3.12 (dd, A$_1$B$_1$X, 1H), 2.90 (dd, A$_1$B$_1$X, 1H), 2.67 (br s, 2H), 2.54 (dd, A$_2$B$_2$X, 1H), 2.38 (dd, A$_2$B$_2$X, 1H), 1.45 (s, 9H).

Example 14

Bcl-2 Binding Assay

Measurement of competition of compounds of the invention with Bim26-mer for a Bcl-2 homologue binding site.

Alphascreen (Amplified Luminescent Proximity Homogenous Assay) is a bead based technology which measures the interaction between molecules. The assay consists of two hydrogel coated beads which, when bought into close proximity by a binding interaction, allow the transfer of singlet oxygen from a donor bead to an acceptor bead.

Upon binding and excitation with laser light at 680 nm, a photosensitizer in the donor bead converts ambient oxygen to a more excited singlet state. This singlet oxygen then diffuses across to react with a chemiluminescer in the acceptor bead. Fluorophores within the same bead are activated resulting in the emission of light at 580-620 nm.

Screening of the compounds of the invention was performed using the Alphascreen GST (glutathione s-transferase) detection kit system. Test compounds were titrated into the assay which consisted of GST tagged Bcl$_w$ ΔC29 protein (0.05 nM Final concentration) and Biotinylated Bim BH3-26 peptide, Biotin-DLRPEIRIAQELRRIGDEFNETYTRR (3.0 nM Final concentration). For the GST tagged BCl-x$_L$ assay, GST tagged BCl-x$_L$ ΔC25 protein (0.6 nM Final concentration) and Biotinylated Bim BH3-26 peptide, Biotin-DLRPEIRIAQELRRIGDEFNETYTRR (5.0 nM final concentration) were used. To this reaction mix anti-GST coated acceptor beads and Streptavidin coated donor beads, both at 15 μg/ml Final concentration, were added and the assay mixture incubated for 4 hours at room temperature before reading. Similarly when the Bcl-2 protein was Mcl-1, GST tagged Mcl-1 protein (0.4 nM Final concentration) and Biotinylated Bak BH3 peptide, Biotin-PSST-MGQVGRQLAIIGDDINRRYDSE-OH (4.0 nM Final concentration) were used.
Detailed Protocol:
1) prepare a 384 well with 4.75 µL of buffer and 0.25 µL of compounds (20 mM in DMSO) per well.
2) Mix the binding partners, in one tube add Bcl-w, BCl-$x_L$ or Mcl-1 and the acceptor beads, in the second tube add Biotinylated BH3 peptide and the donor beads.
3) Pre-incubate the two pairs of binding partners for 30 minutes.
4) Add 1 µL of acceptor beads:Bcl-w, BCl-$x_L$ or Mcl-1 protein mix to each well.
5) Seal the plate and incubate at room temperature for 30 minutes.
6) Add 10 µL of donor bead:BH3 peptide mix to each well.
7) Seal the plate, cover with foil and incubate for 4 hours.

Assay buffer contained 50 mM Hepes pH 7.4, 10 mM DTT, 100 mM NaCl, 0.05% Tween and 0.1 mg/ml casein. Bead dilution buffer contained 50 mM Tris, pH 7.5, 0.01% Tween and 0.1 mg/ml casein. The final DMSO concentration in the assay was 0.5%. Assays were performed in 384 well white Optiplates and analyzed on the PerkinElmer Fusion alpha plate reader (Ex680, Em520-620 nM).

The GST Alphascreen detection kit and Optiplates were purchased from PerkinElmer.

Alphascreen results for the compound of the invention are as follows: of Example 1 indicated an $IC_{50}$ of about 3 nM for Bcl-xL.

| Compound | Bcl-xl | Mcl-1 | Bcl-w |
|---|---|---|---|
| 1 | 0.007 | 9 | nt |
| 2 | 0.006 | 50 | nt |
| 3 | 0.034 | 6 | 3 |
| 4 | 0.016 | nt | 0.8 |
| 5 | 0.003 | 7 | nt |
| 6 | 0.003 | 20 | 0.8 |
| 7 | 0.020 | 10 | 3 |
| 8 | 0.029 | 10 | 3 | nt = not tested

Example 15

Cell Viability Assay

The efficacy of the compounds of the present invention can also be determined in cell based killing assays using a variety of cell lines and mouse tumor models. For example, their activity on cell viability can be assessed on a panel of cultured tumorigenic and non-tumorigenic cell lines, as well as primary mouse or human cell populations, e.g. lymphocytes. For these assays, 5,000-20,000 cells are cultured at 37° C. and 10% $CO_2$ in appropriate growth media, eg: 100 µL Dulbecco's Modified Eagle's medium supplemented with 10% foetal calf serum, asparaginase and 2-mercaptoethanol in the case of pre-B Eµ-Myc mouse tumors in 96 well plates. Cell viability and total cell numbers can be monitored over 1-7 days of incubation with 1 nM-100 µM of the compounds to identify those that kill at IC50<10 µM. Cell viability is determined by the ability of the cells to exclude propidium iodide (10 µg/mL by immunofluorescence analysis of emission wavelengths of 660-675 nm on a flow cytometer (BD FACScan). Alternatively, a high throughput calorimetric assay such as the Cell Titre 96 could be used. Aqueous Non-Radioactive Cell Proliferation Assay (Promega) may be used. Cell death by apoptosis is confirmed by pre-incubation of the cells with 50 µM of a caspase inhibitor such as zVAD-fmk.

Neutralisation of both Bcl-xL and Mcl-1 anti-apoptotic proteins in normal cells is required before a cell undergoes apoptosis via the downstream Bax/Bak pathway [Chen et al., 2005; Willis et al., 2005]. A compound that only targets Bcl-xL should not affect normal cells, but could kill certain cancer cells if they rely more on Bcl-xL and less on Mcl-1 for survival. To mirror this, compound 1 was tested for its effect on survival of wild type (wt) mouse embryo fibroblasts (MEFs), Bax/Bak double knockout (BB DKO) MEFs, MEFs that expressed Noxa, and MEFs that expressed Bad. Noxa specifically neutralizes Mcl-1. Hence, MEFs that express Noxa mirror cancer cell types that are reliant on Bcl-xL for survival and should be much more sensitive to killing by a Bcl-xL targeting compound than MEFs where both Bcl-xL and Mcl-1 are protective. Indeed, as shown in FIG. 1A, this proved to be the case for compound 1.

Figure 1B:
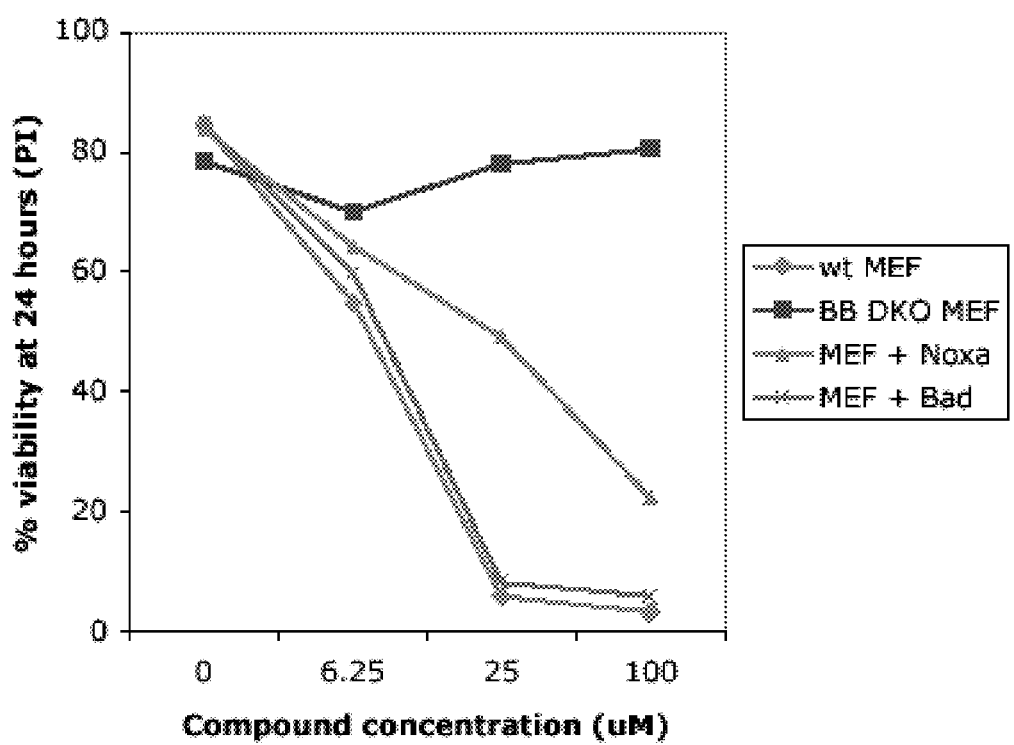

The anticancer drug etoposide also induces cell death via the Bax/Bak pathway, as shown by the resistance of BB DKO MEFs. However, as shown in FIG. 1B it does so less selectively than compound 1.

Example 16

CellTitre-Glow Luminescent Cytotoxicity Assay

Cytoxicity of compounds 1-8 were evaluated on SCLC cell lines NCI-H889, NCI-H1963 and NCI-H146 using Promega CellTitre-Glow luminescent assay kit G7571 according to the following procedures:
Culture Medium and Cell Lines:
1. SCLC cell lines NCI-H889, NCI-H1963, and NCI-H146 were purchased from American Type Culture Collection. Cells were maintained in RPMI 1640 (Invitrogen Corp., Grand Island, N.Y.) supplemented with 10% fetal bovine serum (FBS, Invitrogen), 1% sodium pyruvate, 25 mM HEPES, 4.5 g/L glucose and 1% penicillin/streptomycin (Sigma) in a humidified chamber at 37° C. containing 5% $CO_2$.
2. cells were grown as suspension aggregates in a T162 flask with 25 ml medium and kept at concentration of 1 million/mL.

Test Compound Stocks:
1. test compounds were prepared as 10 mM stocks in DMSO and stored at −20° C.

Test Compound Serial Dilutions:
1. prewarmed medium to 37° C.
2. thawed compounds to room temperature.
3. determined what will be the highest concentration to be tested. (i.e. 10 µM).
4. prepared a 2× stock in culture medium of the first dose (i.e. 2×10 µM=20 µM) in an Eppendorf tube (i.e. 4 µl of 5 mM stock into 1000 µl=20 µM).
5. inverted tube several times to mix.

Serial Dilution in 96 Well Plates:
Compounds were tested in triplicate at concentrations of 10, 5, 2.5, 1.3, 0.63, 0.32, 0.16, 0.08, 0.04 and 0.02 µM. Columns 1-10 comprised the serial test compound treatments, column 11 was the untreated control and column 12 was the 'no cell' control for determining the background.

1. in a 96 well plate was added 50 µl medium/well in columns 2 thru 11 and 100 µl was added to column 12.
2. in column 1 was added 100 µl of 2× compound.

3. made serial dilutions by transferring 50 µl to column 2, and so on up to column 10. After adding 50 µl to column 10 and mixing, discarded 50 µl.
4. stored plates at 37° C. until ready to add cells.

Cell Preparation
1. Cell were washed one time in the culture medium and prepared as a suspension.
   a. cell were first spun down to remove the medium and then ~1 ml 0.25% trypsin was added and gently mixed and incubated for no more than three minutes at room temperature.
   b. ~10 ml of the medium was added and the cells were gently pipetted several times.
   c. cells were then counted and spun down to the volume necessary for the total cell number needed, then resuspended in the medium to 200 cells/µl concentration (50,000 cells/well).
2. 50 µl of cell prep was added to the appropriate wells.
3. incubated cells for 48 hr at 37° C.

CellTiter-Glow Luminescent Assay (Promega—kit G7571):
1. buffer thawed in a 37° C. water bath until thawing completed and then left for at least ½ hr at room temperature
2. substrate and buffer were mixed together and inverted gently several times to dissolve substrate.
3. cell culture plates were removed from the incubator and allowed to adjust to room temperature for at least 15 min.
4. 100 ul of reagent was added to 100 ul culture medium and mixed on plate shaker for 2 min at RT.
5. Incubated for 15 min on bench
6. luminescence was read on BioTek plate reader (sensitivity=95).
7. average background value was calculated (column 12)
8. average background counts was subtracted from all other wells (columns 1-11)
9. average untreated control value was calculated (column 11)
10. test compound treated well values (rows 1-10) were divided by the average control value and expressed as an EC50.

| compound | H146 (EC50 µM) | H889 (EC50 µM) | H1963 (EC50 µM) |
| --- | --- | --- | --- |
| 1 | 0.61 | 0.21 | 0.17 |
| 3 | 3.7 | 1.3 | 1.4 |
| 4 | 0.63 | 0.82 | 0.40 |
| 5 | 0.54 | 0.41 | 0.17 |
| 6 | 0.71 | 0.72 | 0.30 |
| 7 | 1.2 | 0.60 | 0.46 |
| 8 | 1.1 | 1.6 | 0.71 |

REFERENCES

The references listed below, and any others in this specification, should not be taken as, an acknowledgment, or any form of suggestion, that they form any part of the prior art or the common general knowledge in Australia or elsewhere.

L. Chen et al., *Mol. Cell*, 2005, 17, 393-403.
S. Cory, J. A. Adams, *Cancer Cell*, 2005, 5-6.
T. W. Green and P. Wuts, Protective Groups in Organic Synthesis, John Wiley & Sons, 3rd Edition, 1999.
M. G. Hinds, M. Lackmann, G. L. Skea, P. J. Harrison, D.C. S. Huang, C. L. Day, *EMBO J.* 2003, 22, 1497.
X. Liu, S. Dai, Y. Zhu, P. Marrack, J. Kappler, *Immunity.* 2003, 19, 341.
S. W. Muchmore, M. Sattler, H. Liang, R. P. Meadows, J. E. Harlan, H. S. Yoon, D. Nettesheim, B. S. Chang, C. B. Thompson, S. L. Wong, S. L. Ng, S. W. Fesik, *Nature.* 1996, 381, 335.
T. Oltersdorf, S. W. Elmore, A. R. Shoemaker, R. C. Armstrong, D. J. Augeri, B. A. Belli, M. Bruncko, T. L. Deckwerth, J. Dinges, P. J. Hajduk, M. K. Joseph, S. Kitada, S. J. Korsmeyer, A. R. Kunzer, A. Letai, C. Li, M. J. Mitten, D. G. Nettesheim, S. Ng, P. M. Nimmer, J. M. O'Connor, A. Oleksijew, A. M. Petros, J. C. Reed, W. Shen, S. K. Tahir, C. B. Thompson, K. J. Tomaselli, B. Wang, M. D. Wendt, H. Zhang, S. W. Fesik, S. H. Rosenberg, *Nature*, 2005, 435, 677-681.
G. A. Patani and E. J. LaVoie, *Chem. Rev.*, 1996, 96, 3147-3176.
A. M. Petros, J. Dinges, D. J. Augeri, S. A. Baumeister, D. A. Betebenner, M. G. Bures, S. W. Elmore, P. J. Hajduk, M. K. Joseph, S. K. Landis, D. G. Nettlesheim, S. H. Rosenberg, W. Shen, S. Thomas, X. Wang, I. Zanze, H. Zhang, S. W. Fesik, *J. Med. Chem.* 2006, 49, 656-663.
A. M. Petros, D. G. Nettesheim, Y. Wang, E. T. Olejniczak, R. P. Meadows, J. Mack, K. Swift, E. D. Matayoshi, H. Zhang, C. B. Thompson, S. W. Fesik, *Protein Science.* 2000, 9, 2528.
M. Sattler, H. Liang, D. Nettesheim, R. P. Meadows, J. E. Harlan, M. Eberstadt, H. S. Yoon, S. B. Shuker, B. S. Chang, A. J. Minn, C. B. Thompson, S. W. Fesik, *Science.* 1997, 275, 983.
Wang et al., *Proc. Nat. Acad. Sci.*, 2000, 97, 7124.
Wendt et al., *J. Med. Chem.*, 2006, 49, 1165.
S. N. Willis et al., *Genes Dev.*, 2005, 19, 1294-1305.
J. Y. Zhang, *Nature Reviews/Drug Discovery* 2002, 1, 101.

We claim:
1. A compound of formula (I):

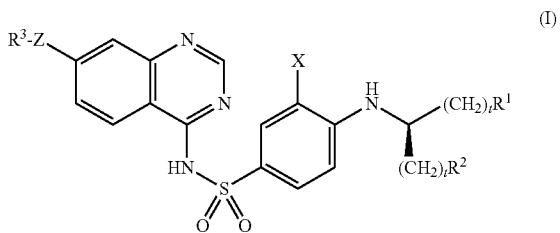

wherein
X is $NO_2$ or $-SO_2-C(X')_3$ wherein X' is H or halo;
Z is a cycloalkyl, cycloalkenyl, aryl, heterocyclic or heteroaryl group;
$R^1$ and $R^2$ are independently aryl, heteroaryl, $-NR^5R^6$, $-CONR^5R^6$, $-O(CH_2)_r$aryl, $-O(CH_2)_r$heteroaryl, $-CO(CH_2)_r$aryl, $-CO(CH_2)_r$heteroaryl, $-CO_2(CH_2)_r$aryl, $-CO_2(CH_2)_r$heteroaryl, $-OCO(CH_2)_r$aryl, $-OCO(CH_2)_r$heteroaryl, $-S(CH_2)_r$aryl, $-S(CH_2)_r$heteroaryl, $-SO(CH_2)_r$aryl, $-SO(CH_2)_r$heteroaryl, $-SO_2(CH_2)_r$aryl or $-SO_2(CH_2)_r$heteroaryl;
$R^3$ is alkyl, alkenyl, $-(CH_2)_r$cycloalkyl, $-(CH_2)_r$cycloalkenyl, $-(CH_2)_r$aryl, $-(CH_2)_r$heterocyclyl or $-(CH_2)_r$heteroaryl, wherein each cycloalkyl, cycloalkenyl, aryl, heterocyclyl and heteroaryl may be optionally substituted with alkyl, alkenyl, halo, nitro, haloalkyl, or phenyl optionally substituted with 1, 2 or 3 alkyl, alkenyl, alkoxy, halo or nitro groups;

R⁵ and R⁶ are independently hydrogen, alkyl or alkenyl or R⁵ and R⁶ taken together with the nitrogen to which they are attached form a heterocyclic or heteroaryl ring;

each R⁷ is independently hydrogen, —$C_{1-6}$alkyl, —$C_{2-6}$alkenyl, —$C_{2-6}$alkynyl or acyl;

each R⁸ is independently hydrogen or halogen;

each R⁹ is independently hydrogen, —$C_{1-6}$alkyl, —$C_{2-6}$alkenyl or —$C_{2-6}$alkynyl, t is 0 or an integer 1 to 6; and r is 0 or an integer 1 to 6;

wherein each alkyl, alkenyl, alkynyl, cycloalkyl, cycloalkenyl, aryl, heterocyclyl and heteroaryl group may be optionally substituted;

or a pharmaceutically acceptable salt thereof.

2. A compound according to claim 1, wherein X is $NO_2$ or —$SO_2$—$CF_2X'$ wherein X' is F or Cl.

3. A compound according to claim 1, wherein X is —$SO_2$—$CF_2Cl$.

4. A compound according to claim 1, wherein Z is a piperazin-1-yl.

5. A compound according to claim 1, wherein R¹ is aryl, heteroaryl, —S(CH₂)ᵣaryl, or —S(CH₂)ᵣheteroaryl.

6. A compound according to claim 1, wherein R¹ is —Sphenyl.

7. A compound according to claim 1, wherein the moiety —(CH₂)ᵣR¹ is —CH₂—S-phenyl.

8. A compound according to claim 1, wherein R² is —NR⁵R⁶ or —CONR⁵R⁶.

9. A compound according to claim 1, wherein in —NR⁵R⁶ or —CONR⁵R⁶, R⁵ and R⁶ together with the nitrogen atom to which they are attached form a heterocyclic or heteroaromatic ring.

10. A compound according to claim 1, wherein the group —(CH₂)ᵣR² is —CH₂CH₂(N-azepanyl), —CH₂CH₂(N-oxazapanyl), —CH₂CH₂(N-pyrrolidinyl), —CH₂CH₂(N-7-azabicyclo[2.2.1]heptanyl), —CH₂CH₂(N-2oxa-5-azabicyclo[2.2.1]heptanyl).

11. A compound according to claim 1, wherein the group —(CH₂)ᵣR² is —CH₂CH₂N(CH₃)₂.

12. A compound according to claim 1, wherein the group —(CH₂)ᵣR² is —CH₂CH₂(N-morpholine).

13. A compound according to claim 1, wherein R³ is:

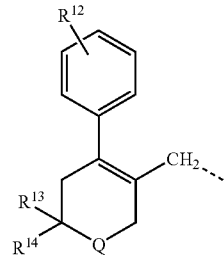

wherein Q is O, CH₂, C(alkyl)₂ or CH₂CH₂; R¹² is halo; and R¹³ and R¹⁴ are both H or are both alkyl.

14. A compound according to claim 1, wherein said compound is selected from one of

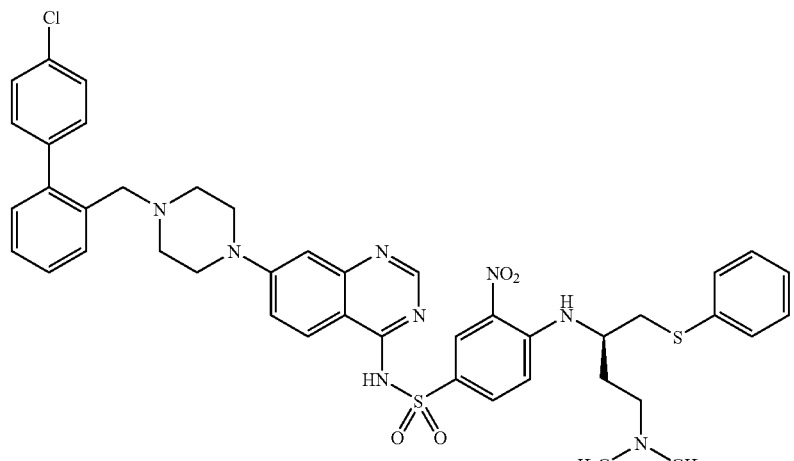

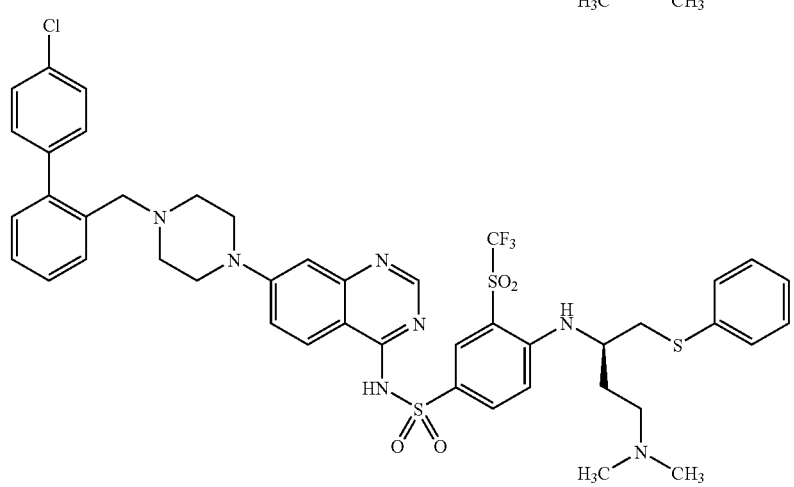

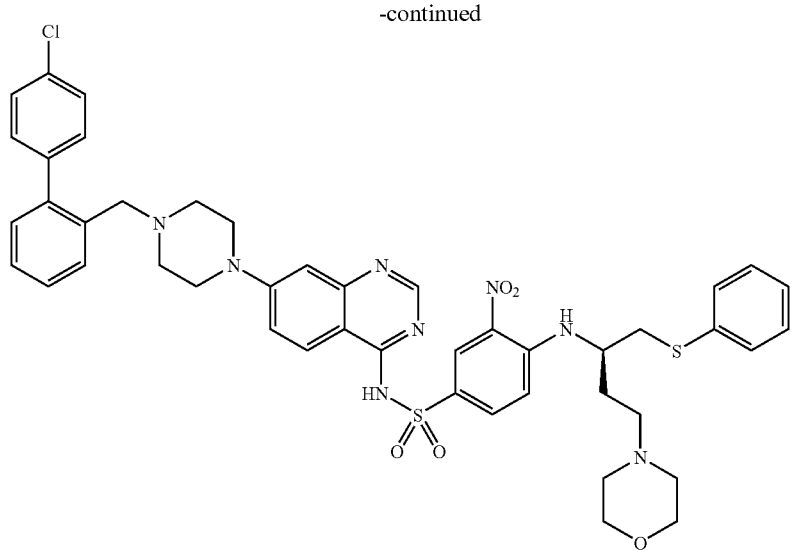
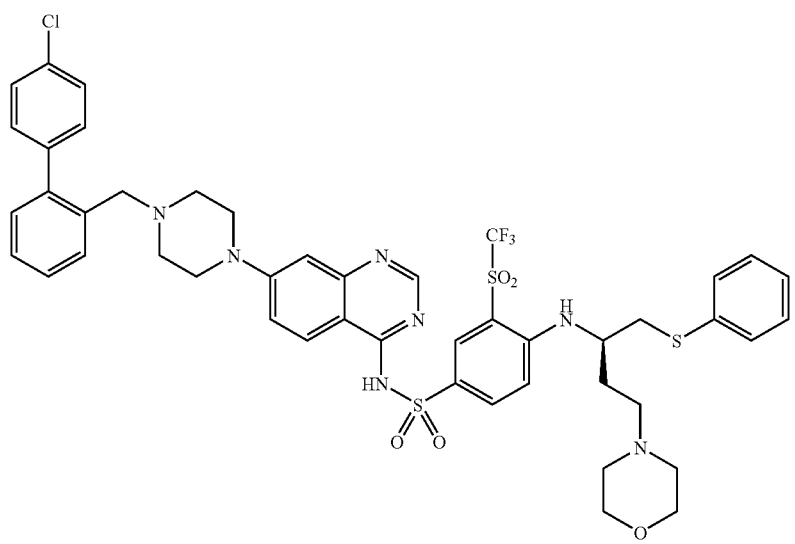
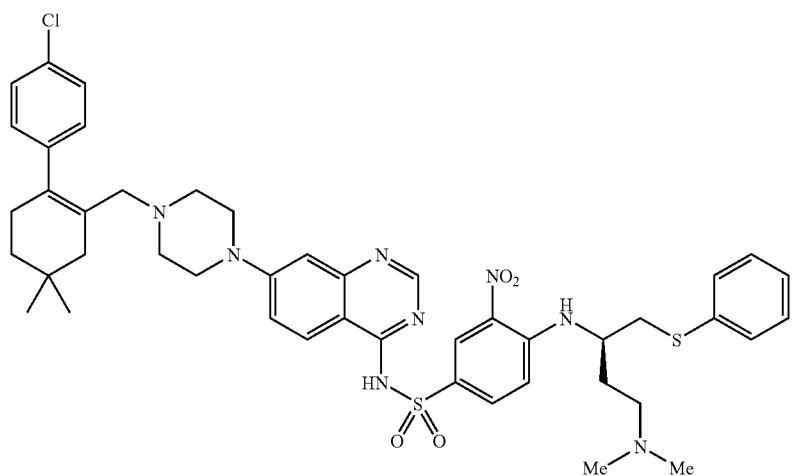

-continued
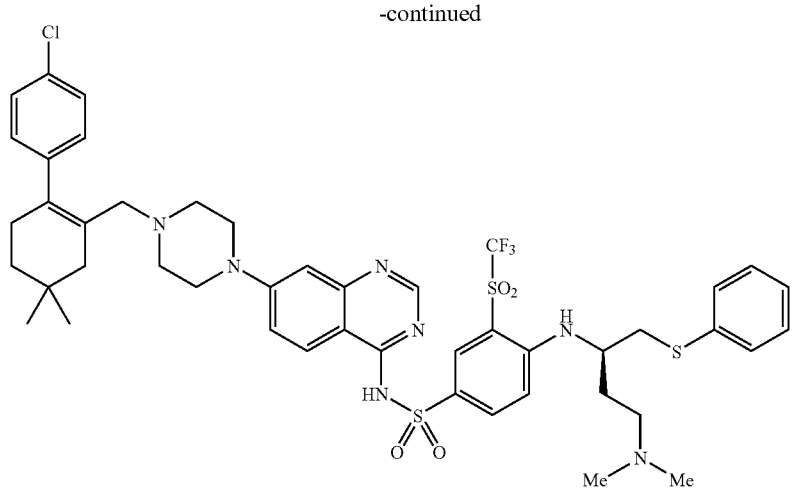
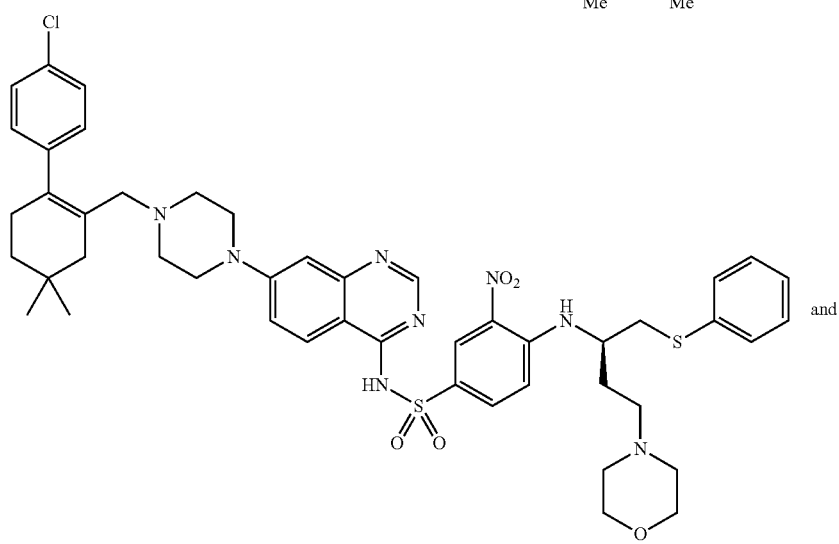
and
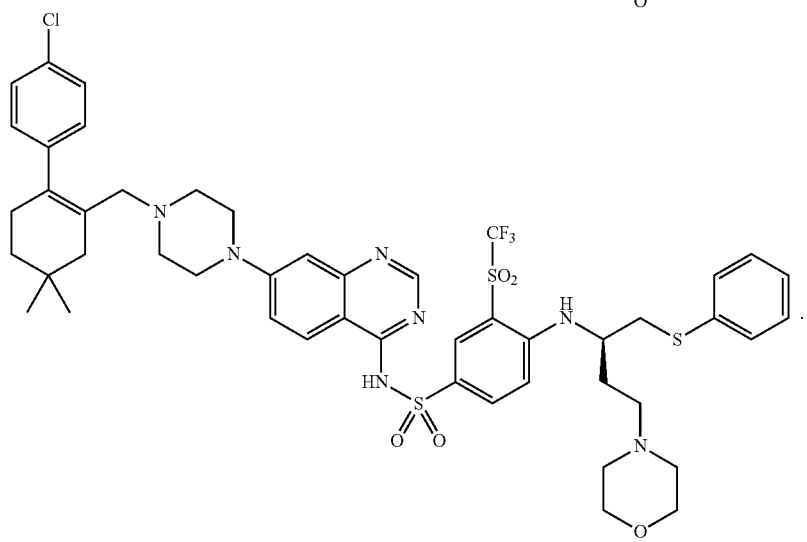
.
15. A pharmaceutical composition comprising a compound of formula (I) as defined in claim 1 and at least one pharmaceutically acceptable carrier.
* * * * *